(12) United States Patent
Zhang et al.

(10) Patent No.: US 11,582,511 B2
(45) Date of Patent: Feb. 14, 2023

(54) RADIO FREQUENCY SENSING IN A TELEVISION ENVIRONMENT

(71) Applicant: QUALCOMM Incorporated, San Diego, CA (US)

(72) Inventors: Xiaoxin Zhang, Sunnyvale, CA (US); Rishabh Raj, Jamshedpur (IN); Parthiban Ellappan, Virudhunagar (IN)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 17/201,497

(22) Filed: Mar. 15, 2021

(65) Prior Publication Data

US 2022/0295144 A1 Sep. 15, 2022

(51) Int. Cl.
*H04N 21/442* (2011.01)
*H04B 17/309* (2015.01)
*H04N 21/45* (2011.01)

(52) U.S. Cl.
CPC ..... *H04N 21/44218* (2013.01); *H04B 17/309* (2015.01); *H04N 21/44204* (2013.01); *H04N 21/4532* (2013.01)

(58) Field of Classification Search
CPC ....... H04N 21/44218; H04N 21/44204; H04N 21/4532; H04N 21/42201; H04N 21/4436; H04N 21/6582; H04B 17/309; A61B 5/0015; A61B 5/05; A61B 5/1176; A61B 5/168; A61B 5/4809; G06F 3/011; G06F 3/012; G06F 3/013; G01S 13/56
See application file for complete search history.

(56) References Cited

U.S. PATENT DOCUMENTS

| | | | |
|---|---|---|---|
| 9,265,438 B2 | 2/2016 | Weinstein et al. | |
| 9,665,169 B1 | 5/2017 | Dai et al. | |
| 9,753,131 B2 | 9/2017 | Adib et al. | |
| 2013/0152113 A1* | 6/2013 | Conrad | H04N 21/42203 725/12 |

(Continued)

FOREIGN PATENT DOCUMENTS

| | | |
|---|---|---|
| KR | 20160022163 A | 2/2016 |
| WO | WO 2020146476 A1 | 7/2020 |

OTHER PUBLICATIONS

Adib, et al. "3d Tracking via Body Radio Reflections", NSDI'14: Proceedings of the 11th USENIX Conference on Networked Systems Design and Implementation, Apr. 2, 2014, pp. 317-329.

(Continued)

*Primary Examiner* — John R Schnurr
(74) *Attorney, Agent, or Firm* — Qualcomm Incorporated

(57) ABSTRACT

Techniques are provided for performing radio frequency (RF) sensing to determine the viewing status of a television user. This can be used to determine user behavior during the playback of content (e.g., whether a user is watching the content), which can be used as a data point for determining the user's level of interest in the content. Using the status of the television user, embodiments can provide additional or alternative functionality, such as powering down and/or powering up the television. Furthermore, RF sensing may be performed by existing television hardware, such a Wi-Fi transceiver, and may therefore provide RF sensing functionality to a television with little or no added cost.

37 Claims, 10 Drawing Sheets

(56) References Cited

U.S. PATENT DOCUMENTS

| | | | |
|---|---|---|---|
| 2014/0150002 A1* | 5/2014 | Hough | H04N 21/2668 |
| | | | 725/9 |
| 2019/0052926 A1* | 2/2019 | Waterman | H04N 21/47217 |
| 2019/0208456 A1* | 7/2019 | Mofidi | H04W 40/02 |
| 2019/0215562 A1* | 7/2019 | Scavo | G01V 3/12 |
| 2020/0302478 A1* | 9/2020 | Martinez | G06Q 30/0255 |
| 2020/0319324 A1* | 10/2020 | Au | G01S 7/006 |
| 2021/0360317 A1* | 11/2021 | Neerbek | H04N 21/44218 |
| 2021/0360318 A1* | 11/2021 | Neerbek | H04H 60/45 |
| 2022/0083120 A1* | 3/2022 | Ghoshal | G06F 1/3215 |

OTHER PUBLICATIONS

Adib, et al. "Capturing the Human Figure Through a Wall", ACM Transactions on Graphics, Oct. 26, 2015, Article No. 219, https://doi.org/10.1145/2816795.2818072.

Adib, et al. "Smart homes that monitor breathing and heart rate", Proceedings of the 33rd Annual ACM Conference on Human Factors in Computing Systems, Apr. 18, 2015 pp. 837-846, https://doi.org/10.1145/2702123.2702200.

International Search Report and Written Opinion—PCT/US2022/070318—ISA/EPO—dated Apr. 25, 2022.

Wang F., et al., "Joint Activity Recognition and Indoor Localization With WiFi Fingerprints", IEEE Access, vol. 7, Jul. 2, 2019 (Jul. 2, 2019), pp. 80058-80068, XP011732885, DOI: 10.1109/ACCESS.2019.2923743 [retrieved on Jun. 28, 2019] abstract section III, section V.A.

\* cited by examiner

RADIO FREQUENCY SENSING IN A TELEVISION ENVIRONMENT

1. FIELD OF INVENTION

The present invention relates generally to object or motion detection, and more particularly, to the use of radio frequency (RF) sensing of an object or motion in a television environment.

2. DESCRIPTION OF RELATED ART

With the ever-increasing sophistication of televisions, consumers are able to stream content from a vast number of content providers. Content providers can further customize content based on user profile information and behavior. Despite the sophistication of modern-day televisions, however, gathering user behavior is often limited to viewing history and inputs during playback (pausing, rewinding, fast forwarding, etc.). These crude mechanisms are generic to all viewers and provide little information to content providers. And although televisions could incorporate cameras to view user behavior during playback, such integration could increase the cost of these televisions and raise privacy concerns for consumers.

BRIEF SUMMARY

Embodiments described herein address these and other issues by providing RF sensing to determine the status of a television user. This can be used to determine user behavior during the playback of content (e.g., whether a user is watching the content), which can be used as a data point for determining the user's level of interest in the content. Using the status of the television user, embodiments can provide additional or alternative functionality, such as powering down and/or powering up the television. Furthermore, RF sensing may be performed by existing television hardware, such a Wi-Fi transceiver, and may therefore provide RF sensing functionality to a television with little or no added cost.

An example method of radio frequency (RF) sensing of a television user, according to this disclosure, comprises transmitting, with one or more wireless transceivers, a first RF signal. The method also comprises receiving, with the one or more wireless transceivers, a first reflected RF signal may comprise reflections of the first RF signal from one or more objects. The method also comprises determining, from the received first reflected RF signal, first channel state information (CSI) of one or more wireless channels. The method also comprises determining status information based on the first CSI, where the status information may comprise information regarding a viewing status of the television user. The method also comprises performing an action with a television based on the status information.

An example device for radio frequency (RF) sensing of a television user, according to this disclosure, comprises one or more wireless transceivers, a memory, and one or more processing units communicatively coupled with the one or more wireless transceivers and the memory. The one or more processing units are configured to transmit, with one or more wireless transceivers, a first RF signal. The one or more processing units are also configured to receive, with the one or more wireless transceivers, a first reflected RF signal may comprise reflections of the first RF signal from one or more objects. The one or more processing units are also configured to determine, from the received first reflected RF signal, first channel state information (CSI) of one or more wireless channels. The one or more processing units are also configured to determine status information based on the first CSI, where the status information may comprise information regarding a viewing status of the television user; and perform an action with a television based on the status information.

Another example device for of radio frequency (RF) sensing of a television user, according to this disclosure, comprises means for transmitting a first RF signal. The device also comprises means for receiving a first reflected RF signal may comprise reflections of the first RF signal from one or more objects. The device also comprises means for determining, from the received first reflected RF signal, first channel state information (CSI) of one or more wireless channels. The device also comprises means for determining status information based on the first CSI, where the status information may comprise information regarding a viewing status of the television user. The device also comprises means for performing an action with a television based on the status information.

An example a non-transitory computer-readable medium, according to this disclosure, stores instructions for radio frequency (RF) sensing of a television user. The instructions comprise code for transmitting, with one or more wireless transceivers, a first RF signal. The instructions also comprise code for receiving, with the one or more wireless transceivers, a first reflected RF signal may comprise reflections of the first RF signal from one or more objects. The instructions also comprise code for determining, from the received first reflected RF signal, first channel state information (CSI) of one or more wireless channels. The instructions also comprise code for determining status information based on the first CSI, where the status information may comprise information regarding a viewing status of the television user. The instructions also comprise code for performing an action with a television based on the status information.

Figure 1:
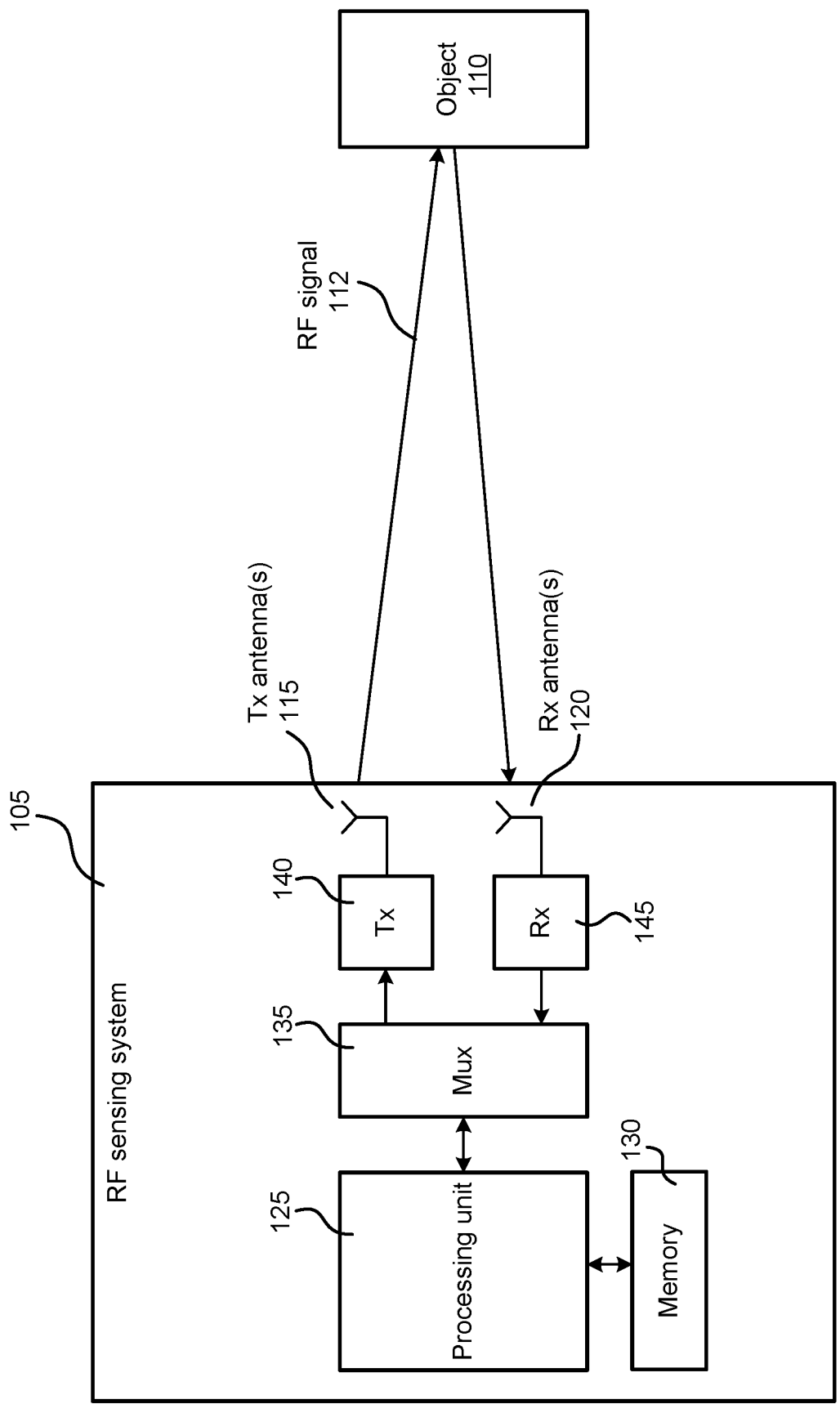
FIG. 1 is a block diagram of an example radio frequency (RF) sensing system capable of performing RF sensing in a television environment.

Like reference symbols in the various drawings indicate like elements, in accordance with certain example implementations. In addition, multiple instances of an element may be indicated by following a first number for the element with a letter or a hyphen and a second number. For example, multiple instances of an element 110 may be indicated as 110-1, 110-2, 110-3 etc. or as 110a, 110b, 110c, etc. When referring to such an element using only the first number, any instance of the element is to be understood (e.g., element 110 in the previous example would refer to elements 110-1, 110-2, and 110-3 or to elements 110a, 110b, and 110-c).

DETAILED DESCRIPTION

The following description is directed to certain implementations for the purposes of describing the innovative aspects of this disclosure. However, a person having ordinary skill in the art will readily recognize that the teachings herein can be applied in a multitude of different ways. Some examples in this disclosure may be based on wireless local area network (WLAN) communication according to the Institute of Electrical and Electronics Engineers (IEEE) 802.11 wireless standards, including those identified as Wi-Fi technologies. However, the described implementations may be implemented in any device, system or network that is capable of transmitting and receiving radio frequency (RF) signals according to any communication standard, such as any of the IEEE 802.11 standards, the Bluetooth® standard, code division multiple access (CDMA), frequency division multiple access (FDMA), time division multiple access (TDMA), Global System for Mobile communications (GSM), GSM/General Packet Radio Service (GPRS), Enhanced Data GSM Environment (EDGE), Terrestrial Trunked Radio (TETRA), Wideband-CDMA (W-CDMA), Evolution Data Optimized (EV-DO), 1xEV-DO, EV-DO Rev A, EV-DO Rev B, High Speed Packet Access (HSPA), High Speed Downlink Packet Access (HSDPA), High Speed Uplink Packet Access (HSUPA), Evolved High Speed Packet Access (HSPA+), Long Term Evolution (LTE), AMPS, or other known signals that are used to communicate within a wireless, cellular or internet of things (IoT) network, such as a system utilizing 3G, 4G, 5G, 6G, or further implementations thereof, technology.

As used herein, an "RF signal" comprises an electromagnetic wave that transports information through the space between a transmitter (or transmitting device) and a receiver (or receiving device). As used herein, a transmitter may transmit a single "RF signal" or multiple "RF signals" to a receiver. However, the receiver may receive multiple "RF signals" corresponding to each transmitted RF signal due to the propagation characteristics of RF signals through multipath channels. The same transmitted RF signal on different paths between the transmitter and receiver may be referred to as a "multipath" RF signal.

As noted, RF signals can be used in RF sensing. RF signals with relatively high frequencies, such as 2.4 GHz, 5 GHz, or 6 GHz (commonly used in implementations of WLAN) have sufficiently small wavelengths to offer resolution capable detecting the presence of an object (e.g., based on volume occupied by the object and/or movement made by the object) and identifying the object. Moreover, such RF sensing can be implemented by existing Wi-Fi/ IEEE 802.11/WLAN transceivers used for communications. It is therefore possible to implement RF sensing with little or no added cost to televisions with these types of existing transceivers. RF sensing may even be implemented in televisions already in the field by means of a firmware update. That said, RF sensing may be achieved by additional or alternative transceivers. For example, according to some embodiments, transceivers may be located in a separate device communicatively coupled with the television (referred to herein as a "connected device"), such as a set-top box, television streaming device (e.g., ROKU®, Google Chromecast™ device, Amazon Fire TV®, etc.). videogame system or the like.

FIG. 1 is a block diagram of an example RF sensing system 105 capable of performing RF sensing in a television environment as described herein. In brief, the RF sensing system 105 uses one or more RF signals comprising one or more waveforms, sequences, or packets to determine the presence and/or movement of an object. This can be done by using RF signals for channel capture, performing channel estimation to obtain a Channel Impulse Response (CIR), a Channel Frequency Response (CFR), and/or other forms of Channel State Information (CSI) indicative of the presence and/or movement of the object. The CSI is indicative of aspects of the RF signals such as multipath, reflections, and signal strength of each path. More broadly, CSI may represent the combined effect of, for example, scattering, fading, and power decay with distance. According to some embodiments, channel estimation used in forms of wireless communication systems can be used obtain CSI. (In wireless communication, CSI is used to properly demodulate and decode a received packet.) Thus, embodiments can leverage existing channel estimation techniques can be leveraged to obtain CSI for RF sensing purposes.

More specifically, the RF sensing system 105 can obtain CSI associated with RF signal 112, reflected from object 110. According to some embodiments, the RF sensing system 105 can use the CSI to calculate a distance and an angle of arrival corresponding to the reflected signal received by Rx antenna(s) 120. For instance, the RF sensing system 105 can determine distance by calculating a time of flight for the reflected signal based on the difference between a leakage signal (not illustrated) and the reflected signal. In further examples, the RF sensing system 105 can determine an angle of arrival by utilizing an antenna array (e.g., RX antenna(s) 120) to receive the reflected signals and measuring the difference in received phase at each element of the antenna array.

As indicated in more detail hereafter, the RF sensing system 105 can utilize the distance and/or an angle of arrival corresponding a reflected signal to detect a presence or movement of an object (e.g. television user) at a location and/or a user's head orientation, eyeball orientation, body position, etc.

In some embodiments, the RF sensing system 105 may utilize artificial intelligence or machine learning algorithms to perform motion detection, object classification, detect head/eyeball orientation, and/or body position determination. In some examples, the machine learning techniques can include supervised machine learning techniques such as those that utilize neural networks, linear and logistics regression, classification trees, support vector machine, any other suitable supervised machine learning technique, or any combination thereof. For instance, a dataset of sample RF sensing data can be selected for training of the machine learning algorithms or artificial intelligence.

The RF sensing techniques described herein may be performed irrespective of their association with a Wi-Fi network. For example, the RF sensing system 105 can utilize its Wi-Fi transmitter and Wi-Fi receiver to perform RF sensing as discussed herein when it is not associated with any access point or Wi-Fi network.

Figure 10:
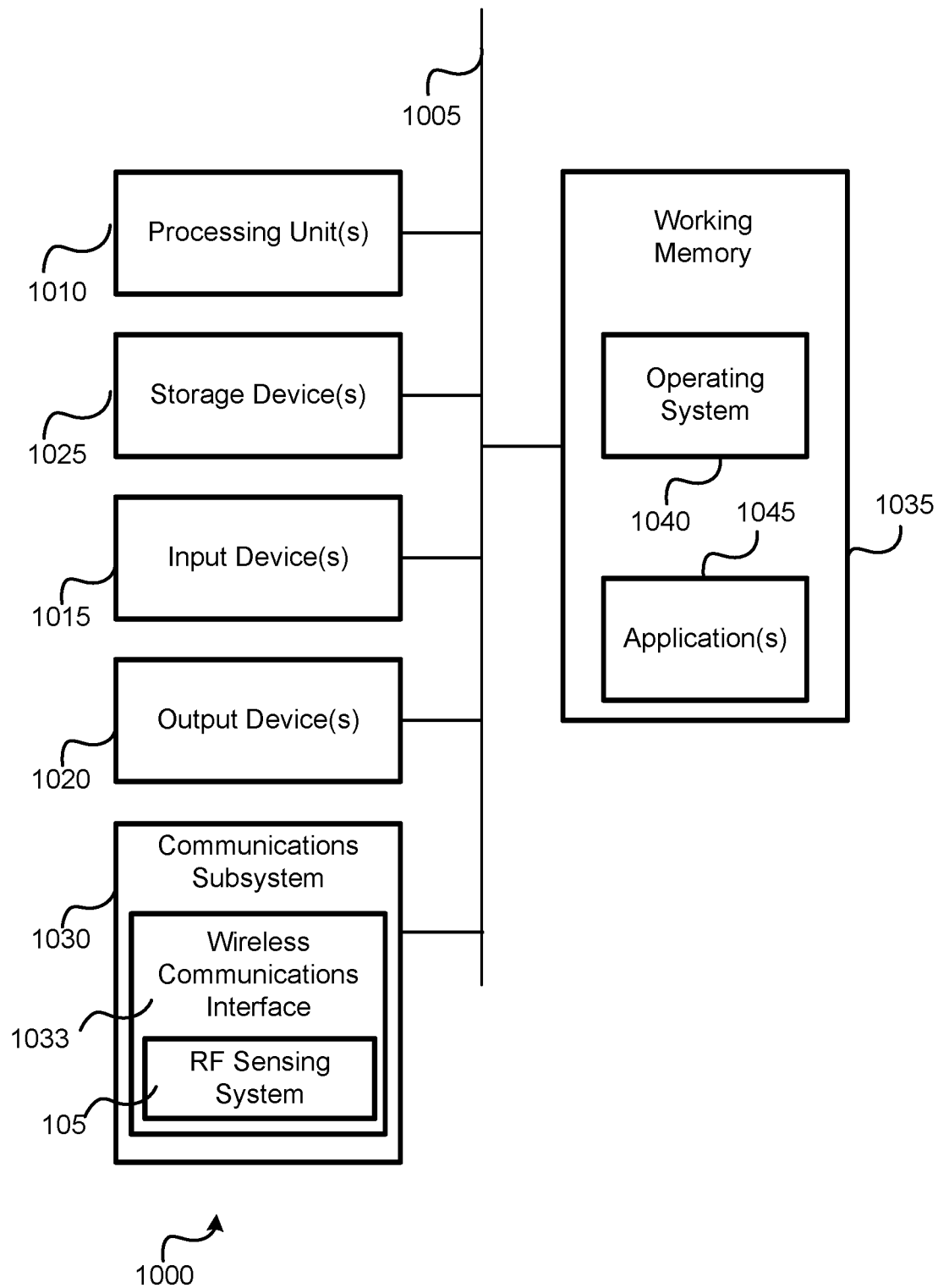
FIG. 10 is a block diagram of an embodiment of a computer system, which can be utilized in embodiments as described herein.

The RF sensing system 105 may comprise a standalone device or may be integrated into a television or connected device. The RF sensing system 105 can, for example, be integrated into a WLAN radio of the television or connected device. Example components of an electronic device comprising an RF sensing system are illustrated in FIG. 10 and discussed in detail hereafter. As noted in more detail below, some embodiments may be implemented such that RF signals are transmitted by one device and received by another.

Generally speaking, with regard to the functionality of the RF sensing system 105 in FIG. 1, the RF sensing system 105 can detect an object 110 by generating RF signal (e.g., comprising one or more pulses) transmitted by one or more Tx antennas 115 that reflect off of the object 110 and are received by one or more Rx antennas 120. The received signals can then be processed by the RF sensing system 105 using digital signal processing (DSP) techniques (including leakage cancellation) to determine the object's presence and/or range. The process of transmitting, receiving, and processing signals is generally referred to herein as an RF sensing "scan." As discussed in more detail herein, the frequency or periodicity of scans may vary depending on a type of transmission mode (e.g., low-resolution or high-resolution scanning), but often may be several times per second.

In some embodiments, an RF sensing system 105 may have a plurality of Rx antennas 120. WLAN radios, for example, commonly have 2 to 4 antennas. In such embodiments, CSI received at different Rx antennas 120 can be used to determine angular information (e.g., by using Rx beamforming, determining angular information phase differences, or the like). In some implementations, embodiments with two antennas have achieved angular granularity of 10° to 15°, for example, and embodiments with four antennas have achieved granularity of 2° to 3°. Moreover, in some other embodiments, an RF sensing system 105 may have a plurality of Tx antennas 115. WLAN radios, for example, commonly have 2 to 4 antennas. In such embodiments, the phase of the Tx antennas can be configured to transmit the RF signal in a beam pointing at a certain direction. In some implementations, embodiments with two Tx antennas have achieved angular granularity of 10° to 15°, for example, and embodiments with four Tx antennas have achieved granularity of 2° to 3°. Changes in CSI over time (e.g., from one scan to the next) are indicative of motion of the object 110. Here changes may comprise changes in amplitude or phase of CSI. Additionally or alternatively, changes may comprise changes in the metrics extracted and/or estimated from CSI, such as time of flight and angle of each reflected path, etc. Thus, RF signals can be used to determine object location, volume, and movement.

This functionality of the RF sensing system 105 is enabled through the use of a processing unit 125, memory 130, multiplexer (mux) 135, Tx processing circuitry 140, and Rx processing circuitry 145. The RF sensing system 105 may include additional components not illustrated, such as a power source, user interface, or electronic interface.

It can be noted, however, that these components of the RF sensing system 105 may be rearranged or otherwise altered in alternative embodiments, depending on desired functionality. Moreover, as used herein, the terms "transmit circuitry," "Tx circuitry," or "Tx processing circuitry" refer to any circuitry utilized to create and/or transmit RF signal. Likewise, the terms "receive circuitry," "Rx circuitry," or "Rx processing circuitry" refer to any circuitry utilized to detect and/or process the RF signal. As such, "transmit circuitry" and "receive circuitry" may not only comprise the Tx processing circuitry 140 and Rx processing circuitry 145 respectively, but also may comprise the mux 135 and processing unit 125. In some embodiments, the processing unit 125 may compose at least part of a modem and/or wireless communications interface (e.g., wireless communications interface 1033 of FIG. 10, described hereinafter). In some embodiments, more than one processing unit may be used to perform the functions of the processing unit 125 described herein. Additionally, although Tx antenna(s) 115 and Rx antenna(s) 120 are illustrated as being separate antennas, some embodiments may use the same one or more antennas for transmission and reception.

The Tx processing circuitry 140 and Rx processing circuitry 145 may comprise subcomponents for respectively generating and detecting RF signals. As a person of ordinary skill in the art will appreciate, the Tx processing circuitry 140 may therefore include a pulse generator, digital-to-analog converter (DAC), a mixer (for up-mixing the signal to the transmit frequency), one or more amplifiers (for powering the transmission via Tx antenna(s) 115), etc. The Rx processing circuitry 145 may have similar hardware for processing a detected RF signal. In particular, the Rx processing circuitry 145 may comprise an amplifier (for amplifying a signal received via Rx antenna(s) 120), a mixer for down-converting the received signal from the transmit frequency, an analog-to-digital converter (ADC) for digitizing the received signal, and a pulse correlator providing a matched filter for the pulse generated by the Tx processing circuitry 140. The Rx processing circuitry 145 may therefore use the correlator output as the CIR, which can be processed by the processing unit 125 (or other circuitry) for leakage cancellation, for example. Other processing of CSI obtained from the RF signal may also be performed, such as object detection, range, motion, direction of departure (DoD) or direction of arrival (DoA) estimation.

It can be noted that the properties of the transmitted RF signal 112 may vary, depending on the technologies utilized. As previously indicated, techniques provided herein can apply to WLAN technologies, which typically operate at 2.4, 5, and 6 GHz, but may include frequencies ranging from 900 MHz to 60 GHz. (That said, some embodiments may utilize RF frequencies outside this range.) This includes, for example, frequencies utilized by the 802.11ad Wi-Fi standard (operating at 60 GHz). Because RF sensing may be performed in the same frequency bands as communication, hardware may be utilized for both communication and RF sensing. For example, one or more of the components of the RF sensing system 105 shown in FIG. 1 may be included in a wireless modem (e.g., Wi-Fi or 5G modem) of a television. That said, embodiments may utilize an RF sensing system 105 independent of any such communication means. As noted, for example, some embodiments may utilize Ultra-Wideband (UWB) transceivers. Techniques for RF sensing described may utilize various types of RF signal, such as Zadoff sequences, Orthogonal Frequency-Division Multiplexing (OFDM) Long Training Field (LTF)-like symbols for channel capture to determine the presence and/or movement of the object 110. Because the RF sensing system may be capable of sending RF signals for communication (e.g., using 802.11 communication technology), embodiments may leverage channel estimation used in communication to obtain CSI for performing RF sensing as provided herein. In Wi-Fi, channel estimation may be done by using Legacy Long Training Field (L-LTF) and High Throughput (HT)/Very High Throughput (VHT)/High-Efficiency Long Training Field (HE-LTF) in a communication packet preamble. Embodiments may use a similar approach, for example, by using a known transmitted signal for channel estimation.

Accordingly, RF signal may comprise the same wireless pulses and/or packets as those used for channel estimation in communication.

As noted, embodiments herein are directed toward RF sensing in a television environment, enabling televisions (and/or connected devices) to provide additional functionality, such as determining user interest in television content, automatically powering-up the television, and/or powering down the television. All while avoiding the privacy concerns, hardware costs, and power consumption that the use of a camera may entail.

Figure 2:
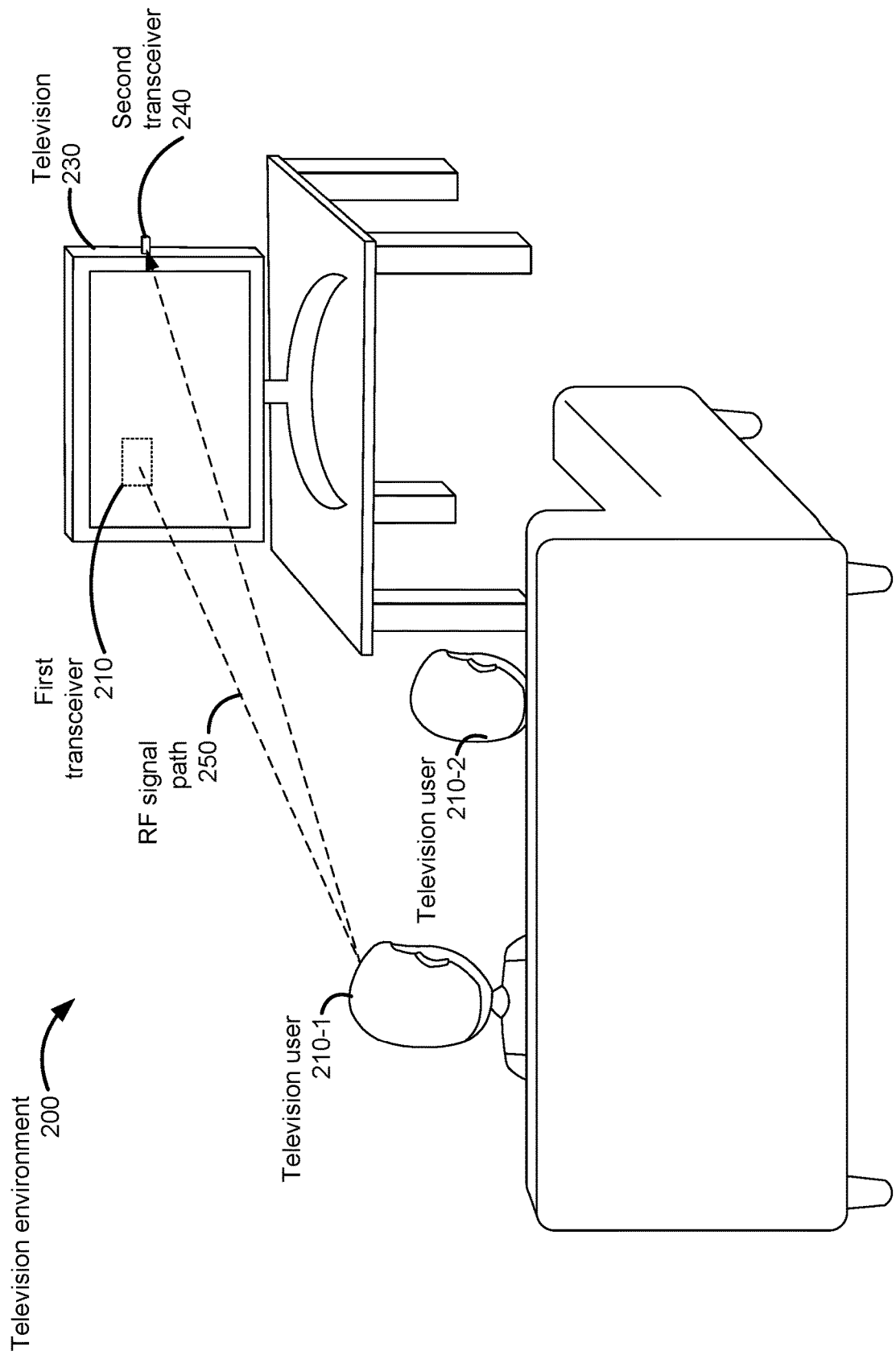
FIGS. 2 and 3 are perspective views of example television environments.

FIG. 2 is a perspective view of an example television environment 200, illustrating how RF sensing may be used to detect one or more television users 210-1, 210-2 (collectively and generically referred to herein as television users 210), according to an embodiment. Here, a first transceiver 220, which may comprise an RF sensing system 105 incorporated into the circuitry of television 230, may transmit RF signals that reflect off objects in the television environment 200 and are received by a second transceiver 240 (illustrated as a media streaming device plugged into the television 230). The location of the first transceiver 210 is illustrated with a dotted line, illustrating an example location, behind the television's display, the first transceiver 210 may be housed within the television. A processor or computer communicatively coupled with the first transceiver 210 and second transceiver 240, such as a processor internal to the television 230, may coordinate the timing of the transmittal and receipt of the RF signals. The first transceiver 210 and second transceiver 240 may be communicatively linked with and/or incorporated into electrical hardware of the television 230. As previously noted, example electrical hardware is illustrated in FIG. 10 and described in more detail below.

As a specific example of how a first television user 210-1 is detected, portions of the RF signals that travel along an RF signal path 250 reflect off the first television user 210-1. Reflections of these RF signals are received by the second transceiver 240. As previously noted, these reflections may be identified in the captured RF sensing data, such as CSI, and used to determine the presence of the television user 210-1 by comparing RF sensing data (comprising the captured CSI and/or information derived therefrom) with previously-obtained RF sensing data (e.g., from CSI captured during a calibration procedure) in which the television user 210-1 is not present. The presence of a human user may be determined, for example, based on CSI-derived information indicative of the detection of a human-sized object (based on one or more dimensions of the object), which may be verified during calibration as a human user. Additionally or alternatively, motion of the first television user 210-1 can be detected by determining a change in successively-captured RF sensing data (e.g., from successive scans). Such changes may include, for example, a change in amplitude of CSI, phase of CSI, angle extracted from CSI, time of flight extracted from CSI, Doppler extracted from CSI, or any combination thereof. Furthermore, RF sensing data of RF signals having multiple spatial streams and/or relatively high bandwidth can be used to determine objects and/or smaller motions and/or finer detail then RF sensing data of RF signals having fewer spatial streams and/or relatively low bandwidth.

It can be noted that the configuration illustrated in FIG. 2 is provided as a non-limiting example. Additionally or alternatively, the second transceiver 240 external to the television may transmit RF signals, and the first transceiver 210 may receive the reflected RF signals. Alternative configurations may have multiple transceivers external to the television 230, multiple transceivers internal television 230, or any combination of internal/external transceivers. Furthermore, although described herein generically as "transceivers," alternative embodiments may utilize transmitters and/or receivers in the manner described herein.

Figure 3:
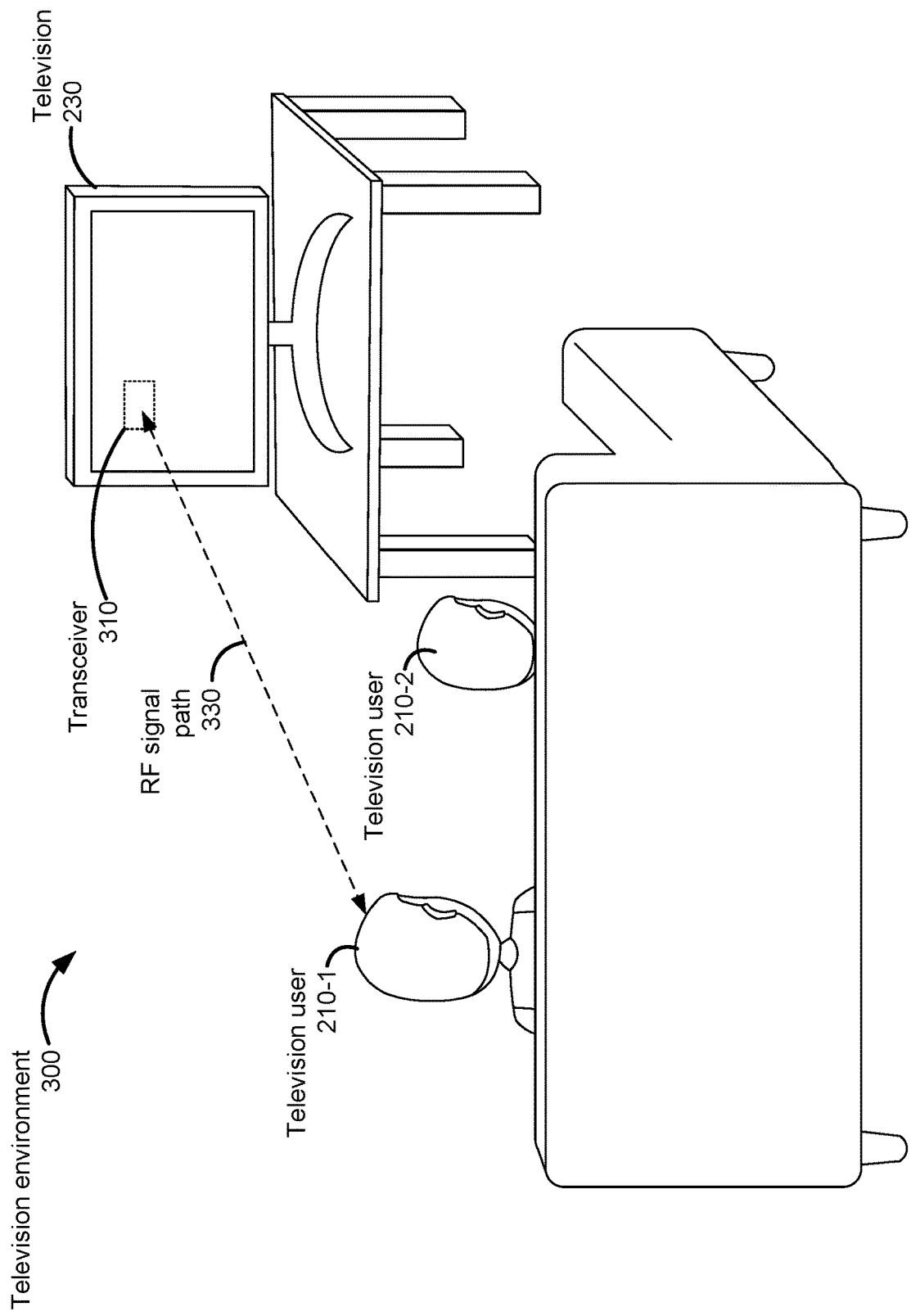

FIG. 3 is a perspective view of an example television environment 300, similar to FIG. 2, illustrating how RF sensing may be performed according to another embodiment. Here, rather than having separate transceivers, the television 230 has a single transceiver 310. In this embodiment, the transceiver 310 may comprise an RF sensing system 105 and may perform the functions of both first transceiver 210 and second transceiver 220 of FIG. 2, transmitting and receiving RF signals and processing RF signals reflected off of the television user 210-1 that travel along RF signal path 330 (as well as processing reflected signals from other objects). A person of ordinary skill in the art will appreciate, because the transceiver 310 may perform both transmit and receive functions at the same time, the transceiver 310 may implement leakage mitigation and/or similar algorithms to help minimize interference between the transmit and receive functions. Thus, in the television environment 200 of FIG. 2, channel capture (between the first transceiver 210 and second transceiver 240) can be used to capture CSI and perform RF sensing, while in the television environment 300 of FIG. 3, a single transceiver 310 can capture CSI and perform RF sensing.

Whether in a single-transceiver environment (e.g., television environment 300 of FIG. 3) or multi-transceiver environment (e.g., television environment 200 of FIG. 2), the determination of the presence of the first television user 210-1 and differentiation of the first television user 210-1 with the second television user 210-2 and other objects may be achieved, in part, through calibration and filtering. For example, the television 230 may guide an authorized user (e.g., a user authorized to change television settings and/or otherwise manage the television) to perform calibration of the transceiver(s) to recognize reflections of RF signals from television users 210 (e.g., in locations in which they are viewing the television 230) and ignore reflections of RF signals from other objects (pets, tables, chairs, etc.). After calibration, RF sensing can be performed by comparing RF sensing data (e.g., CSI) from reflections of RF signals with RF sensing data in obtained during calibration to identify the presence of television users 210. Additional details regarding calibration are provided in reference to FIGS. 4A-4C.

Figure 4A:
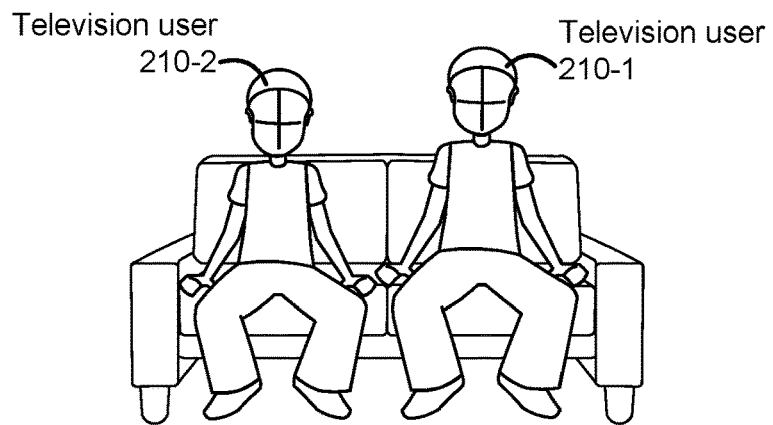
FIGS. 4A-4C are illustrations of television users in a television environment from the perspective of the television, according to an embodiment.
Figure 4B:
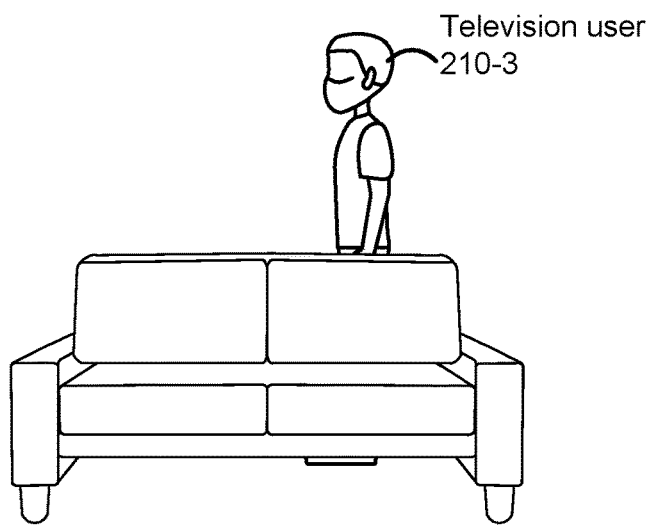
Figure 4C:
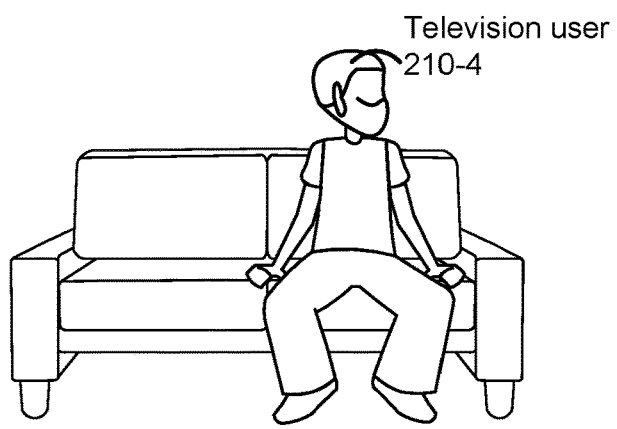

FIGS. 4A-4C are figures of television users 210 in the television environment 200 of FIG. 2 from the perspective of the television 230 (not shown). As noted, the television 230 may not be equipped with a camera, so the television may not "see" the television users 210 in the manner illustrated in FIGS. 4A-4C. However, as noted, RF sensing in the manner described herein is capable of enabling a determination of movement in the television environment, the presence of one or more television users 210 and other objects, and a status or state of the one or more television users 210. This can be done by leveraging information obtained during a calibration process.

During calibration, the television may guide a television user 210 and/or other authorized user (e.g., using an on-screen menu) through a process in which RF sensing data, such as CSI or CIR, is obtained while the television user 210 is at a viewing location and in a viewing position. FIG. 4A, for example, illustrates a situation similar to FIG. 2 in which two users 210-1 and 210-2 sitting on a couch with heads directed toward the television. During calibration (which may be performed for one user at a time), television users 210 may sit in/near these locations in similar positions. RF sensing data comprising the CSI or information derived therefrom (e.g., volume information of the television user 210) can then be compared with corresponding RF sensing data from CSI obtained at a subsequent time to determine whether users are in a desired location and/or in a desired position at the subsequent time.

Calibration may entail capturing CSI from a user at various different locations and in various different positions. An individual television user 210, for example, may be asked to sit at different positions in which they typically watch television. This can enable the television (or other device performing the RF sensing) to, during subsequent operation, identify instances in which one or more television users 210 are watching television (e.g., as in FIG. 4A) and disregard television users in scenarios such as the one illustrated in FIG. 4B in which a television user 210-3 is at a different location.

Embodiments may further identify situations, such as the situation illustrated in FIG. 4C, in which a television user 210-4 is at a location in which the television user 210-4 may watch television, but not in a position that indicates television is being watched. Here, for example, the television users head is rotated to the side, and thus attention of the television users 210-4 is likely not on the content played by the television. According to some embodiments, these situations may be detected by simply detecting a difference in RF sensing data while the television user 210-4 is in this position with corresponding RF sensing data from the CSI obtained during calibration (while the television user 210-4 was in an "attentive position" watching TV, similar to the position of the television users 210 in FIG. 4A). As noted, such data can include, for example measurements of multipath, reflections and signal strength of each path. Variance in one or more of these measurements beyond a threshold amount (e.g., a certain percentage) from corresponding measurements obtained during calibration while the television user 210-4 was in an "attentive position" may result in a determination that the use is not in an attentive position. Additionally or alternatively, according to some embodiments calibration may include obtaining RF sensing data from CSI of the television user 210-4 in various "inattentive" positions (e.g., head to the side or down), indicative of the television user 210-4 not watching television, and situations such as the situation illustrated in FIG. 4C can be identified based on a comparison of (currently) obtained RF sensing data from CSI to the RF sensing data from CSI obtained while the television user 210-4 was not in an attentive position.

It can be noted, however, that although some embodiments may have a calibration process in which CSI is obtained while a television user 210 is at various locations and in various positions (e.g., attentive and inattentive position), other embodiments may leverage crowdsourcing and/or machine learning to capture a minimal amount of CSI. That is, a service provider (e.g., TV manufacturer) may obtain CSI information from many thousands or even millions of television users 210. Using this information, the service provider may develop processing algorithms capable of "extrapolating" information from a minimal set of CSI. For example, using CSI from thousands of television users 210 in "attentive" and "inattentive" positions, a service provider may train a machine learning algorithm to identify "inattentive" positions of television users based on a basic "attentive" position of the television users obtained during calibration. The machine learning algorithm could then be used in subsequently-manufactured televisions (or other devices) and/or propagated to televisions (or other devices) in the field via a firmware update over the Internet.

As previously indicated with regard to the FIG. 1, RF sensing is based on the reflection of RF signals from the surfaces of objects. Based on reflections at different angles (azimuth and elevation) and ranges the object's location and volume can be determined. As noted, this can be used not only to determine whether a television user 210 is in a particular location, but also may be used to determine whether a television user is in a position that indicates he or she is watching the television. Higher-resolution implementations can obtain higher resolution RF scans capable of obtaining additional information. Implementations operating at 5 GHz or 6 GHz, for example, may be capable of determining the dimensions of a television user's head, torso, and limbs from captured CSI. Implementations using 60 GHz, for example, may be capable of determining an eyeball position of a television user. As such, calibration may entail additional steps. For example, in embodiments using 60 GHz, calibration may entail capturing CSI while a television user 210 is looking toward the television, and optionally capturing CSI while a television user 210 is looking away from the television.

RF sensing data comprising CSI and/or information extracted from the captured CSI (e.g., volume information, eyeball tracking information, etc.) can be stored in a user profile (e.g., locally by the television and/or in the cloud by a service provider). Because the RF sensing data of different television users 210 can be distinguishably different, it can be used to identify television users 210 and distinguish television users 210 from other objects, such as pets. The calibration for different users and the setting up of different user profiles may be used to allow the television or connected device to identify television users 210 using RF sensing. The creation of a new user profile may be initiated by the authorized user and/or prompted by the television (e.g., upon detecting a new, unrecognized television user at a television viewing location via RF sensing).

Each user profile can include information enabling the television (or other RF sensing device) to identify the user. Thus, this can include RF sensing data comprising captured CSI (e.g., from calibration RF sensing performed when initially creating the user profile) or information derived therefrom, such as volume information. The volume information can include overall volume information (e.g., height, width, etc.) and/or volume of different parts of the user (e.g., head, torso, arms, legs), as well as positions of these volumes. That said, because RF sensing may be capable of sensing more than just volume to identify television users, other types of information used to detect and/or identify television users may be stored. For example, RF sensing may be capable of sensing breathing rates for different users, which may be used, for example, as an additional point of data by which television users may be identified. Moreover, for high-frequency embodiments (e.g., 60 GHz or more), specific facial features may be identified (eyes, nose, mouth, cheeks, etc.) and identification algorithms can be used to recognize a television users face and distinguish it from the faces of other television users. A user profile may further include information on the television environment such as a preferred sitting location of the user with respect to the television environment. The user profile may include a preferred or regular pose for the user when watching television, such as sitting, lying, etc. As noted, when subsequently performing RF sensing (e.g., in the manner discussed in the embodiments shown in FIGS. 5 and 7-9), the RF sensing data obtained during the RF sensing can be compared with corresponding RF sensing data from user profiles to identify a television user.

Additionally, the user profile can include information provided by the user and/or information about the user gathered by the RF sensing device and/or service provider. For example, while creating a user profile for a new user, the television can guide the new user through an on-screen menu that allows the user to input different preferences. According to some embodiments, for example, the on-screen menu may include a series of questions the answers to which can be indicative of user preferences. Moreover, these preferences can impact not only primary television content (movies, TV shows, etc.) but also advertisement content.

According to some embodiments, some user accounts may include child accounts. For example, using a password to initiate a user profile creation process, an authorized (adult) user can create a user profile for a child, providing similar information as would be provided in the creation of a user profile for an adult. However, the authorized user can additionally indicate (e.g., using a non-screen menu item, such as a checkbox, radio button, etc.) that the new user is a child. As such, the television may enable the authorized user to set content filtering, screen time limits, etc. on the child's user account. In subsequent use of the television, if the television senses the child using RF sensing, it can then implement the filtering unless an adult is present and/or provides authorization (e.g., inputs a password) for viewing content otherwise restricted for viewing by the child.

Once user profiles are created, television functionality can be customized to accommodate preferences of one or more users using the television. For example, using RF sensing, one or more users can be identified, and an on-screen menu can be customized to provide content curated based on user preferences. If more than one user is identified, content may be based on the preferences of multiple users (e.g., providing content and/or other menu options that may satisfy preferences for all users). Accordingly, menus and content may be customized for each user and/or combination of users.

As previously noted, a service provider can obtain information from many TVs (thousands, millions, etc.) to perform crowdsourcing based on information provided by users. (Such crowdsourcing may be performed, for example, after receiving permission to do so from individual users, and in compliance with applicable laws regarding protecting consumer information, etc.) Using information obtained from users regarding user preferences and demographic information (gender, age, city/state/country of residence, etc.), a service provider may be able to determine trends among different demographic groups for different types of content. These trends then can be used to provide suggestions for new content for television users in those demographic groups.

As described in various embodiments hereafter, the television (or connected RF sensing device) can perform RF sensing scans at different times to detect the presence of a television user and, optionally, gauge an interest of the television user in content played by the television. The user profile can store RF sensing data obtained during a set up process in which RF sensing is calibrated for the particular television user. Detection of the user may take place when new RF sensing data obtained during subsequent use of the television matches (e.g., is within a threshold degree of similarity, e.g. based on a similarity metric, such as a sum of absolute differences (SAD)) the stored RF sensing data of a user profile. If the new RF sensing data is within a threshold degree of similarity with stored RF sensing data from multiple user profiles, then the user having stored RF sensing data that most closely matches the new RF sensing data may be the one that is detected.

Comparing and matching the new RF sensing data to stored RF sensing data can be done in any of a variety of ways, depending on desired functionality. In some embodiments, for example, one or more "features" can be extracted from the obtained CSI, e.g. an obtained 2D CSI map, which can include the above-described information (e.g., volume, breathing rate, facial features, etc.). These features can be derived from CSI, such as 2D Angle-of-Arrival (AoA) and Time-of-Flight (ToF) data, or similar data. A distance between the measured features of the new RF sensing data and corresponding features from the stored RF sensing data can be determined and a similarity learning algorithm can be used to generate a similarity score. The determination of whether there is a match can be based on whether the similarity score exceeds a threshold value.

A threshold value for the similarity score can be set to minimize false alarm rates while keeping the successful detection rate high. According to some embodiments, there may be multiple thresholds to determine if a similarity score indicates matching (e.g., exceeding a higher similarity value threshold), not matching (e.g., falling below a lower similarity value threshold), or requiring more testing to confirm (e.g., a similarity score falling between the higher and lower similarity value thresholds). According to some initial results, embodiments have been found to achieve lower than 1 in 100,000 false detection rate for more than 99% of time in facial recognition.

Other embodiments may use yet other techniques for matching the new RF sensing data to stored RF sensing data. In some embodiments, for example in cases where processing capabilities allow, machine learning can be used by providing a delta between CSI of the new RF sensing data and CSI of stored RF sensing data into a machine-learning algorithm to determine whether there is a match. Additionally or alternatively filtering can be used to filter out the reflections that are not of interest and focusing on the paths that are reflected by a television user. Interpolation could then be used to recover finer resolution reflections, etc.

Stored RF sensing data may be refined over time, depending on desired functionality. Subsequent calibration can be obtained periodically and/or may be based on a triggering event. In some embodiments, once a user is detected by matching new RF sensing data with stored RF sensing data from the user profile, the values in the stored RF sensing data may be updated based on values from the new RF sensing data (e.g., averaged over time). In this way, RF sensing data can be updated to help ensure accurate data for a user is stored, and to accommodate possible changes in a user, such as a child growing over time. In some embodiments, the television or connected RF sensing device may prompt a user to confirm (e.g., via an interactive television menu) the user's identity, prior to updating the RF sensing data stored in the user's profile. (E.g., "Alice has been detected, please confirm.") In some embodiments, such additional confirmation and calibration may take place, subsequent to an initial calibration for a user profile, until a threshold amount of time has passed (e.g., a few weeks) to help ensure accuracy in the RF sensing data stored in a user profile.

The ability to perform RF sensing in the manner previously described and illustrated in FIGS. 1-4C can enable a television to provide functionality related to object detection and/or movement detection that may otherwise require cameras, which are not only more expensive, but may also compromise the privacy of television users.

One such function is television user interest detection. Content is valued more when it engages the interest of users. As such, playing content that users are interested in provides more value not only to consumers, but also to content providers, including advertisers. With this in mind, RF sensing can be performed during playback of particular content by the television to determine a level of interest that one or more users has in the content being played by the television. This information can be used locally by the television and/or remotely by content providers as feedback to enable the television/content providers to provide content of interest to television users.

Figure 5:
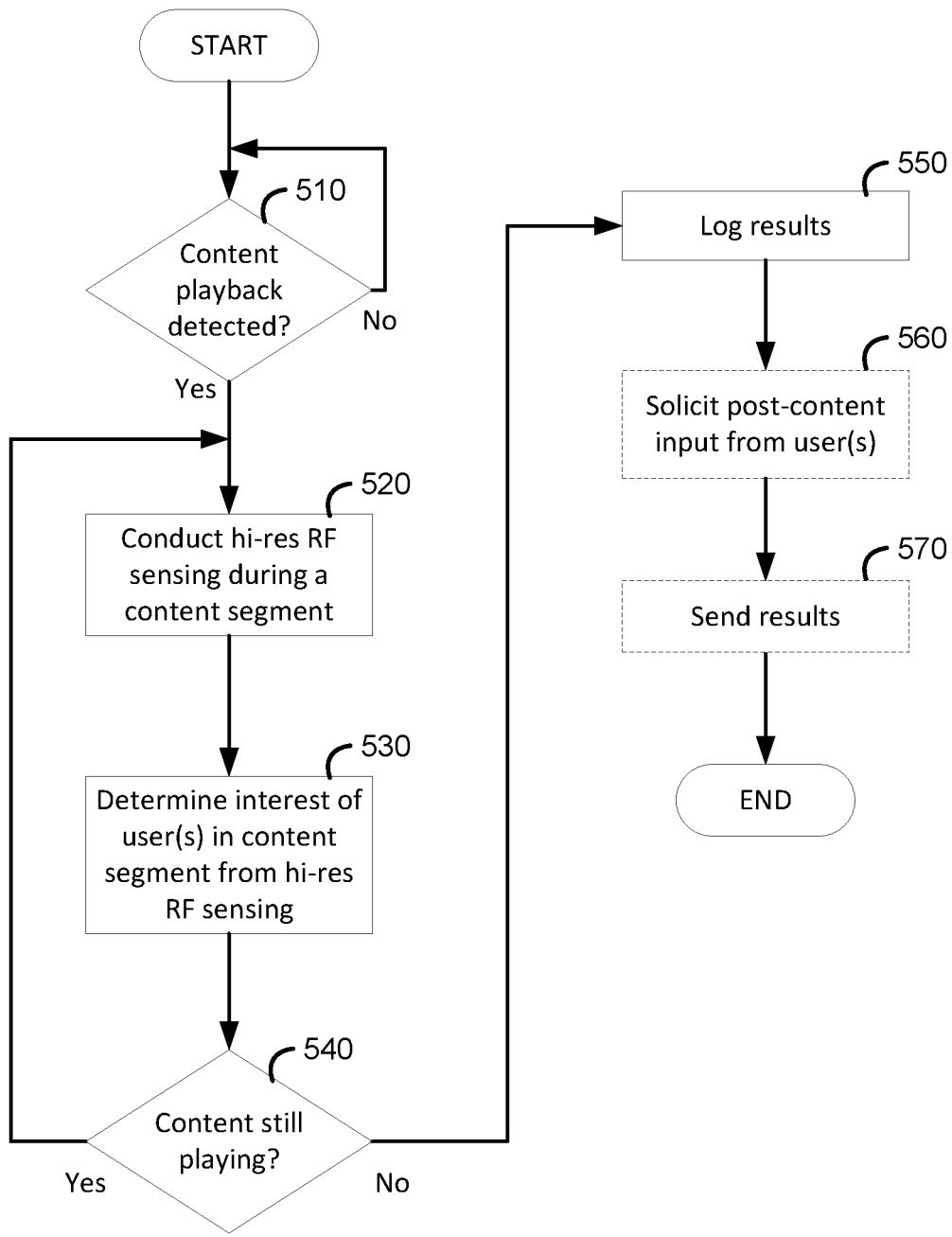
FIG. 5 is a flowchart illustrating a process of determining television user interest in content played by a television, according to an embodiment.

FIG. 5 is a flowchart illustrating a process of determining television user interest in content played by a television, according to an embodiment. As with other figures provided herein, FIG. 5 is provided as a non-limiting example. Alternative embodiments may add, omit, rearrange, and/or otherwise alter the operations illustrated in FIG. 5. The RF sensing provided in the process illustrated in FIG. 5 may be provided by an RF sensing system, such as the one illustrated in FIG. 1, which can be used in one or more transceivers as illustrated in FIGS. 2 and 3. The implementation of the process illustrated in FIG. 5 may be performed by one or more processing units of the television or a connected device. Processors (e.g., processing units) and other example components of a television/connected device are illustrated in FIG. 10 and described hereafter.

The process may begin at block 510, where a determination is made of whether certain content is being playback by the television. Here, the certain content may comprise any content for which user interest is to be determined. Advertisements and other content, such as technical reports, for example, may comprise content for which user interest is to be determined. The type of content may be user-selectable (e.g., in a user menu), and may vary based on desired functionality, user preferences, etc.

The determination of what type of playback is detected can be made based on metadata regarding the media being playback. Videos for Video on Demand (VOD), for example, may include metadata comprising a title, genre, etc. Additionally or alternatively, embodiments may include an explicit data field by which such videos can be flagged for determination of user interest. For advertisements in live data streams, digital "cue tones" in the data streams may indicate periods in the stream in which advertisements can be played back. In response to the cue tones, televisions can play advertisements from an advertisement buffer and/or retrieve advertisements from an advertisement server in real time. If advertisements are a type of content for which user interest is to be determined, some embodiments may include, as part of the process of playing back advertisements, implementing the functionality in FIG. 5 by proceeding to the functionality of block 520.

At block 520, the functionality comprises conducting high-resolution ("hi-res") RF sensing. In current implementations, a low-resolution ("low-res") RF sensing is a mode of RF sensing that captures CSI with a relatively low frequency (e.g., a periodicity of 100 ms or more, alternatively 500 ms or more, alternatively 1 s or more, etc.), relatively low bandwidth (e.g., 20 MHz or less, or 40 MHz or less), and/or relatively few spatial streams (e.g., a single spatial stream). Depending on the frequency/bandwidth/number spatial streams used, low-resolution RF sensing may be capable only of movement detection, although some embodiments may be capable of detecting television users and/or other objects. In contrast, high-resolution RF sensing is an RF sensing mode in which CSI may be captured at a relatively high frequency (e.g., a periodicity of 1 ms or less, alternatively 2 ms or less, alternatively 50 ms or less, etc.), relatively high bandwidth (e.g., 80 MHz or more, or 160 MHz or more), and/or an increased number of spatial streams (e.g., two or more) relative to the number used in low-resolution detection. High-resolution RF sensing (e.g., in the manner performed at block 520 of FIG. 5) may therefore be capable of detecting movement and/or objects with a higher accuracy than low-resolution detection. High-resolution detection can, for example, determine a user's position, including sitting position/pose, head orientation, etc. Moreover, for embodiments using sufficiently high frequencies, high-resolution detection can determine eyeball position of one or more television users.

At block 530, the functionality comprises determining an interest of one or more television users in a segment of content based on the high-resolution RF sensing. As noted, high-resolution RF scanning can be used to determine the location and position of one or more television users. By comparing RF sensing data (CSI or information extracted therefrom) with corresponding data for a user in "inattentive" and "attentive" positions, a television or other electronic device performing the RF sensing can determine a level of interest. For example, multiple scans may be performed (e.g., several times per second) for a given segment of content. If the RF sensing data from most scans during the segment matches RF sensing data obtained during calibration in which the television user was in an "inattentive" position (and/or does not match RF sensing data obtained during calibration in which the television user was in an "attentive" position), then the user can be determined to be uninterested in that segment of content. Alternatively, if a television user is determined to be "attentive" during X % of scans for a segment of content, the television user can be determined to show an X % interest in that segment of content. Additional ways in which user interest can be determined and logged are provided hereafter.

At block 540, the television or other electronic device performing RF sensing determines whether the particular content identified at block 510 is still playing. If so, the process at blocks 520 and 530 can be repeated for each segment of content, until the content is finished playing. Once the content has finished playing, the results can be logged, as indicated at block 550.

Figure 6A:
FIGS. 6A-6C are figures illustrating different ways in which user interest can be logged, according to different embodiments.
Figure 6B:
Figure 6C:

The way in which the results of the RF sensing to determine television user interest are logged can vary, depending on desired functionality. FIGS. 6A-6C are figures illustrating different ways in which user interest can be logged, according to different embodiments.

FIG. 6A illustrates a first type of viewership log 600-A, according to an embodiment. In this embodiment, an entry is made that summarizes viewership interest in content across all segments of content. In the particular example illustrated in FIG. 6A, the content may comprise a 30-second advertisement, broken into 30 one-second segments. The viewership log 600-A provides a cumulative summary in which the number of segments (seconds) for which a television user is determined to be in an "attentive" position are summed, and the sum is included in an entry for that television user. This process is repeated for each detected television user. Depending on desired functionality, a new viewership log 600 may be created for each item of content, and/or a composite viewership log may include entries for multiple items of content.

FIG. 6B illustrates a second viewership log 600-B, similar to the viewership log 600-A illustrated in FIG. 6A. However, rather than including a "Duration of Interest" summary in which segments of content are summed (as included in viewership log 600-A), the viewership log 600-B includes a "Largest Portion of Interest" field that identifies the longest contiguous segment of content (identified by starting and ending times within the content) for which the respective television user was determined to be in an "attentive" position. This can be particularly useful in determining which portion of the content held the television users interest the longest. (An alternative embodiment may, for example, indicate a "Largest Portion of Disinterest" that indicates the longest contiguous portion of the content during which the respective television user was not in an "attentive" position.

FIG. 6C illustrates a third viewership log 600-C indicating a far more comprehensive log then either viewership log 600-A or viewership log 600-B. Here, the viewership log 600-C comprises, for each television user, an indication of whether the respective television user was determined to be "attentive" to each segment of content. In particular, for each segment, attentiveness is indicated with a binary indicator (e.g., where "inattentive" may be indicated as a "0" and "attentive" may be indicated as a "1"). This form of user interest logging, therefore, provides an extensive record of times at which a user is showing interest or disinterest in the content played by the television. In alternative embodiments, a log may provide even more granular details by indicating, for each segment, a percentage or number of scans for which a television user is determined to be "attentive."

It can be noted that the viewership logs 600 shown in FIGS. 6A-6C are provided as non-limiting examples. Alternative embodiments may log television user interest in any of a variety of alternative ways, depending on desired functionality.

Returning to FIG. 5, blocks illustrated by dashed lines show optional functions that may be included in the process. For example, at block 560, the functionality includes soliciting post-content input from the one or more television users viewing playback of the content on the television. This functionality may be included, for example, if the television user(s) are determined to show at least a threshold level of interest in the content. The input solicited from the users can be indicative of the user's interest in the particular content and/or the type of content.

For example, if a television user is determined to be in an "attentive" position for at least a threshold percentage (e.g. 95%) of the duration of a vehicle advertisement, the television can provide one or more prompts to the user (e.g., via an on-screen menu, audio/voice prompt, etc.) to determine how the vehicle advertisement was received. Example prompts could include asking the television user to indicate whether the vehicle advertisement applied to the user, whether the television user would be interested in receiving more advertisements regarding the particular vehicle in the vehicle advertisement (or vehicles of a certain type, or vehicles in general, etc.), and/or whether the television user would be interested in receiving more information regarding the particular vehicle of the vehicle advertisement. In the latter case, if the vehicle user indicates they would like more information, the television may play an additional advertisement, provide a website and/or telephone number regarding the vehicle on the screen, and/or open a web browser to a site that includes sales locations, promotions, and/or other details regarding the vehicle.

At block 570, the process may optionally include sending the results to a remote device. That is, according to some embodiments, the television or connected RF sensing device may be connected to the Internet or other data communication network, and may thereby be capable of sending information regarding television user interest to a remote service provider, such as a television manufacturer, content provider, advertisement provider, etc. This information can include, for example, any logged information regarding user interest (e.g., as shown in viewership logs 600 of FIGS. 6A-6C), along with an identification of the corresponding item of content. Depending on desired functionality, this information can be sent once content has completed playback (or even during playback, as noted below), or in batches (e.g., sending information regarding content viewed, accumulated every hour, every day, every week, etc.). As a result, customized content may be provided to the television. In the case of advertisements, for example, an advertisement server may send more customized advertisements to the television, which the television may store in a buffer and play during periods of time during the playback of other content (e.g., advertisement-supported content) set aside for advertisements. In this way, the buffer can be refreshed with advertisements that more closely match the preferences of the television viewer(s).

It can be noted that, in alternative embodiments, the functionality at blocks 550-570 may be performed as RF sensing is occurring. That is, logging, interest solicitation, and sending results can occur in real time as content is being played back, in addition or as an alternative to performing these functions after playback. In such embodiments, the television and/or remote service can adjust to user interest in real time and, if desired, alter content accordingly.

According to some embodiments, RF sensing may be used to provide additional or alternative functionality. Examples of two such functions are illustrated in FIGS. 7 and 8.

Figure 7:
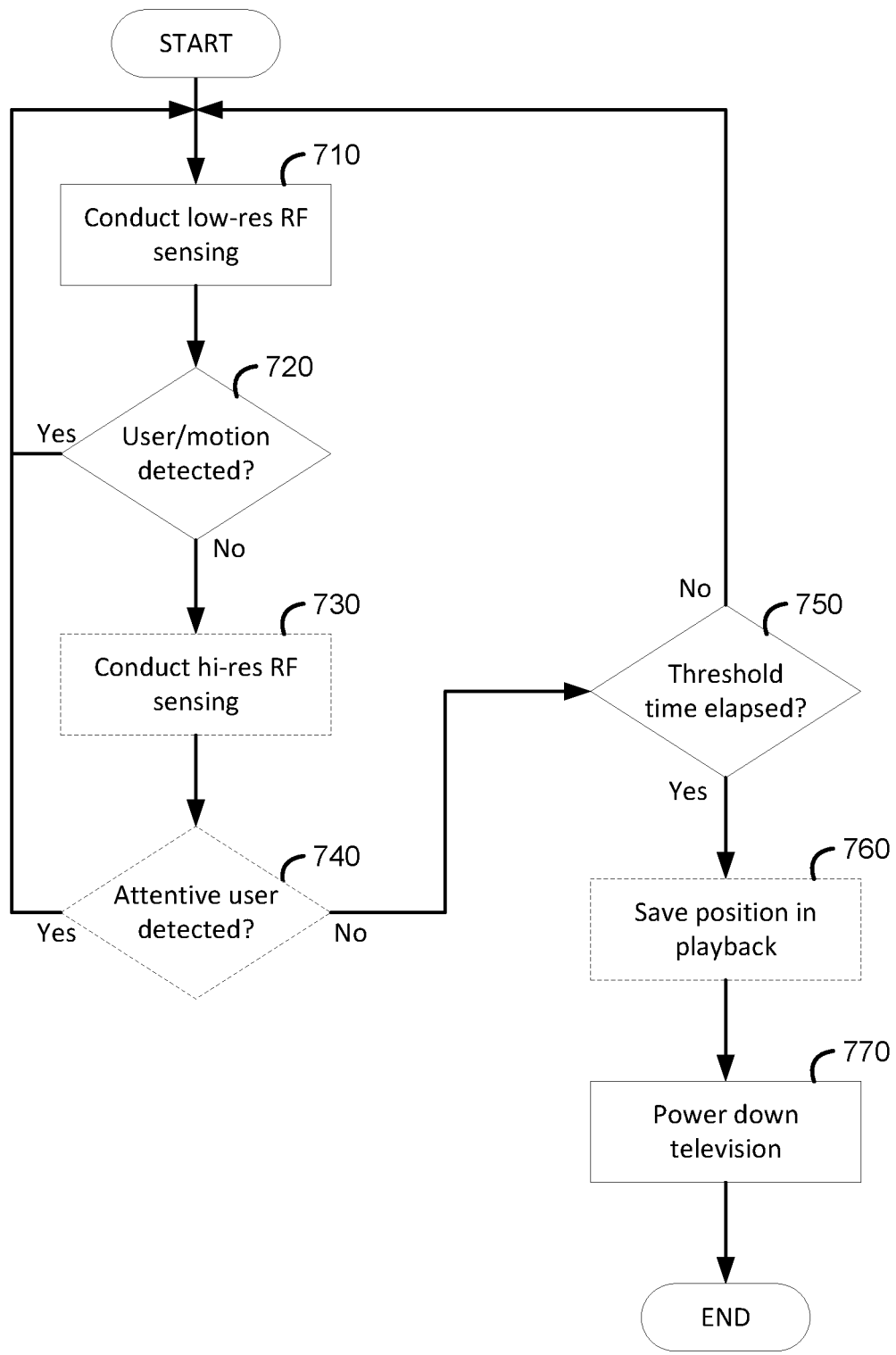
FIG. 7 is a flowchart illustrating a process of powering down a television based on information obtained from RF sensing, according to an embodiment.

FIG. 7 is a flowchart illustrating a process of powering down a television based on information obtained from RF sensing, according to an embodiment. As with other figures provided herein, FIG. 7 is provided as a non-limiting example. Alternative embodiments may add, omit, rearrange, and/or otherwise alter the operations illustrated in FIG. 7. The RF sensing provided in the process illustrated in FIG. 7 may be provided by an RF sensing system, such as the one illustrated in FIG. 1, which can be incorporated into one or more transceivers as illustrated in FIGS. 2 and 3. The implementation of the process illustrated in FIG. 7 may be performed by one or more processing units of television or other electrical device, such as the electrical device illustrated in FIG. 10 and described hereafter.

Figure 8:
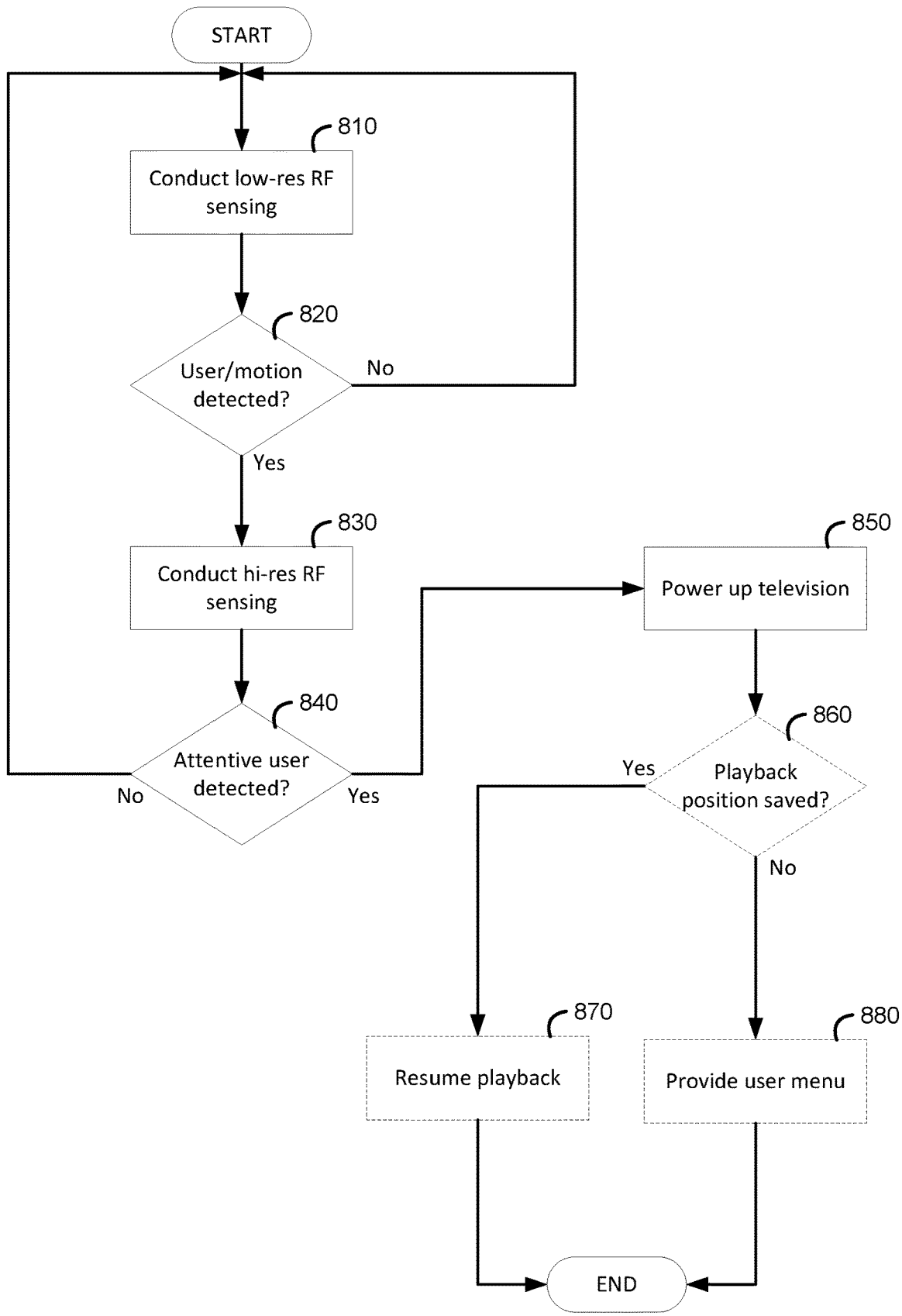
FIG. 8 is a flowchart illustrating a process of powering up a television based on information obtained from RF sensing, according to an embodiment.

It can be noted that the process illustrated in FIG. 7 can begin during content playback by a television and may be compatible with the process illustrated in FIG. 5 (and the process illustrated in FIG. 8 described hereafter). For example, the process in FIG. 5 may be executed during advertisements or other content for which it may be desirable for content providers to obtain user interest. The process in FIG. 7, however, may be a process executed by default, when not executing the process of FIG. 5. Furthermore, the television or other electrical device executing these processes may perform optimizations by, for example, using the RF sensing data obtained in one process in the other. As a specific example, RF sensing data obtained from the high-resolution RF sensing at block 520 may obviate the need to conduct low-resolution RF sensing at block 710. Other such optimizations may be made when performing these (and possibly other) RF sensing processes in parallel.

The functionality at block 700 comprises conducting low-resolution RF sensing. As noted, low-resolution RF sensing may comprise a form of RF sensing that captures CSI with a relatively low frequency (e.g., a periodicity of 100 ms or more, alternatively 500 ms or more, alternatively 1 s or more, etc.), relatively low bandwidth (e.g., 20 MHz or less, or 40 MHz or less), and/or relatively few spatial streams (e.g., a single spatial stream). Because of its relatively low resolution, the RF sensing may not be capable of identifying a particular television user in some embodiments, but the RF sensing may still be capable of detecting motion and/or the presence of a television user at a certain location, which may be sufficient to implement the functionality of the power-down process of FIG. 7. Moreover, because low-resolution RF sensing consumes less power than high-resolution RF sensing, low-resolution RF sensing may be preferable in most cases. That said, alternative embodiments may conduct high-resolution RF sensing. This can be the case, as previously noted, where the television or another RF sensing device performing the functionality in FIG. 7 is performing RF sensing for other functions in parallel.

At block 720, the RF sensing data is analyzed to determine whether any user or motion is detected. As previously noted, RF sensing data may comprise CSI and/or data derived therefrom. Changes in RF sensing data between successive scans can be indicative of motion, and low-resolution RF sensing data may be capable of detecting a human-sized object at a location where television viewing takes place (which may be previously determined based one or more user profiles, in particular from RF sensing data included in the user profiles). As such, a comparison of RF sensing data with corresponding RF sensing data stored in user profiles may not be necessary to perform user/motion detection.

If a user or motion is detected, the process can continue to conduct low-resolution RF sensing (at block 710). Otherwise, the process can optionally perform the function at block 730 by conducting high-resolution RF sensing. This high-resolution RF sensing can be performed to confirm the presence or absence of a television user. This additional confirmation can be performed, for example, to determine the presence of a user in embodiments in which low-resolution sensing is only capable of providing motion detection (without detecting the presence of a motionless user). This can help prevent the instance in which a user is motionless, but still watching television.

If the functionality at block 730 is performed, the process can additionally perform the functionality at block 740, in which a determination is made whether an attentive user is detected based on the RF sensing data obtained at block 730. If an attentive user is detected, the process can revert again to the functionality at block 710 by conducting low-resolution RF sensing. Otherwise, if an attentive user is not detected (e.g., the user is inattentive, no user is present, etc.), the process can proceed to block 750.

The functionality at block 750 comprises determining whether a threshold time has elapsed. If not, the process again reverts to conducting low-resolution RF sensing at block 710. According to some embodiments delay period, which may be user configurable, may pass before the low-resolution RF sensing is repeated. This functionality can help ensure the television is not powered down prematurely. According to some embodiments, this time threshold may be set at a period of time long enough to enable television users to leave the room temporarily (e.g., to get a snack, use the restroom, etc.) or recover from an inattentive state (e.g., in a sleeping position), but short enough to proceed to power the television without leaving it on for an excessive amount of time once it is clear a television user is not going to continue watching television. According to some embodiments, this threshold may be configurable by television users themselves (e.g., via an on-screen user menu).

If a threshold amount of time has elapsed, the process can optionally proceed to the functionality at block 760 by saving a position in playback. This can allow a television user to subsequently resume playback at a position in a television program, movie, etc. where playback was stopped prior to powering down the television. In some embodiments, the position in playback may be saved in the profile of one or more television users most recently identified using RF sensing. This can allow the one or more users to subsequently resume playback, while other television users (who may be presumed not to have an interest in resuming playback at the saved position) may not be given that option.

The process can then proceed to perform the functionality at block 770, by powering down the television. Here, "powering down" the television may comprise powering off the television, or simply powering down the television to a low-power state (in which the television may be capable of subsequently powering up in the fashion described hereafter with regard to FIG. 8). If the process of FIG. 7 is performed by a transceiver of the television or a connected device (e.g., set-top box or streaming device), powering down the television may comprise sending a signal to an application processor or central processing unit of the television to power the television down. A connected device, which may provide a video output via High-Definition Multimedia Interface (HDMI) or Universal Serial Bus (USB), for example, additionally or alternatively may stop providing video output. This can be an additional or alternative indicator to the television to power down.

FIG. 8 is a flowchart illustrating a process of powering up a television based on information obtained from RF sensing, according to an embodiment. As noted, this functionality may be performed in conjunction with the functionality of either or both of the processes illustrated in FIGS. 5 and 7. As with other figures provided herein, FIG. 8 is provided as a non-limiting example, and alternative embodiments may add, omit, rearrange, and/or otherwise alter the operations illustrated in FIG. 8. Similar to the processes illustrated in FIGS. 5 and 7, the RF sensing provided in the process illustrated in FIG. 8 may be provided by an RF sensing system, such as the one illustrated in FIG. 1, which can be incorporated into one or more transceivers as illustrated in FIGS. 2 and 3. The implementation of the process illustrated in FIG. 8 may be performed by one or more processing units of an electrical device, such as the electrical device illustrated in FIG. 10 and described hereafter.

Here, the process may begin with the functionality of block 810, where a low-resolution RF sensing is performed. Similar to the low-resolution RF sensing at block 710 of FIG. 7, the low-resolution RF sensing here may be used to detect the motion and/or presence of a television user. Unlike the RF sensing at block 710 of FIG. 7, however, the low-resolution RF sensing is performed while the television is powered down (e.g., in a low-power state, relative to an active state in which the television is playing content). For many embodiments, this may mean a power budget for performing the low-resolution RF sensing at block 810 (whether performed by internal circuitry of the television itself, or by a connected device, which may draw power from the television or may itself have a strict power budget) may be particularly low. Accordingly, the low-resolution RF sensing performed at block 810 may be customized to suit the power requirements of such a budget. This may mean, for example, performing RF sensing with a sufficiently low resolution to meet the budget, yet performing scans with a scan periodicity, bandwidth, and/or number of streams to sufficiently detect the motion and/or presence of a television user.

At block 820, a determination is made, from RF sensing data obtained from the RF sensing scan performed at block 810, whether the motion and/or presence of any television user is detected. If not, the process can revert back to the functionality at block 810, continuing to perform low-resolution RF sensing. A, possibly user configurable, delay period may pass before the low-resolution RF sensing is repeated. Otherwise, if motion and/or the presence of a television user is detected, the process can continue to the functionality at block 830.

At block 830, the functionality comprises conducting high-resolution RF sensing. Similar to the functionality of block 730 and FIG. 7, the high-resolution scanning performed at block 830 of FIG. 8 can be used to confirm whether a television user or even whether a particular television user is detected. According to some embodiments, this functionality can help reduce the likelihood of a "false positive" detection of a user/motion by the low-resolution sensing which would power up the television. Such instances can include, for example, motion by a pet or cleaning robot, detection of a television user at a location not used for viewing television (e.g., as illustrated in FIG. 4B), detection of a television user in an inattentive position (e.g., as illustrated in FIG. 4C), and/or detection of another human (without a corresponding user profile).

Furthermore, according to some embodiments, the automatic power-up functionality of FIG. 8 may be a user-configurable setting that may be activated on a per-user basis. Moreover, in addition or as an alternative to powering up the television by being in an attentive position (e.g., as shown in FIG. 4A), a television user may configure a unique "power up" pose to power-up the television. This can be done, for example, by allowing a user to select a pose (e.g., which may involve a selected position and/or orientation of the user's head, torso, arms, legs, etc.) during configuration of the user's profile used specifically to automatically power up the television and calibrating the RF sensor to detect that pose by capturing RF sensing data while the user is in the pose. Further, depending on desired functionality, the user further may select a particular location (e.g., a sitting location in the room in which the television is located) in which the "power up" pose may be performed, thereby further reducing the chance that the television is automatically powered-up inadvertently. As such, the high-resolution RF sensing performed at block 830 can be used to identify a particular television user and determine, based on a user profile saved for the television user, whether the user has selected the automatic power-up functionality and/or whether the user is in the user's preconfigured "power up" pose.

At block 840, the functionality comprises determining whether an attentive television user is detected. As noted, this can include determining whether the television user has selected automatic power up functionality and/or is in a personalized/customized "power up" pose. If not, the process can revert back to the functionality of block 810 and continue conducting low-resolution RF sensing. Otherwise, the process can proceed to the functionality of block 850 and power up the television. Here, "powering up" comprises changing the television from a powered-down or low-power state (in which the display, circuitry, and/or other television components may be deactivated or in standby mode) to an active state in which content can be played back.

Once the television is powered up, the process may include performing the functions shown at block 860 and block 870 or 880. The functionality at block 860 includes determining whether a playback position with regard to previously viewed content has been saved. Depending on desired functionality, a playback position may be saved for a particular user or set of users, as previously noted. For such embodiments, block 860 may comprise determining whether a playback position has been saved for a specific user or set of identified users, which may be identified at block 840. As noted, positions in playback may be saved automatically, such as at block 760 in the process illustrated in FIG. 7. By implementing these functions in the processes illustrated in FIGS. 7 and 8, for example, a television may save a position in playback of content and power down in accordance with the process of FIG. 7 when a television user falls asleep (and therefore does not move and/or is not in an attentive position), and subsequently turn back on and resume playback at the saved position after detecting that the television user has returned to an attentive state.

Additionally or alternatively, a television may save a position automatically when a user or set of users stops playback and powers down the television (which may be a functionality a user can select in the television settings, for example), or when the user/set of users manually selects to save a position in playback (e.g., by interacting with an on-screen menu). If a playback position is saved, the television can resume playback, as indicated at block 870. Otherwise, a user menu may be provided to the user, as indicated at block 880.

As noted, because RF sensing can identify a user or set of users watching television, content and/or menus may be customized based on user preferences of the identified user(s). Because one or more users may be identified at block 840, the menu provided at block 880 may be customized in this manner. If only children are identified, for example, a children-friendly menu may be provided. According to some embodiments, if an adult television user is identified via RF sensing and/or an authorized password is entered, the menu may revert from a children-friendly menu to a normal menu.

Figure 9:
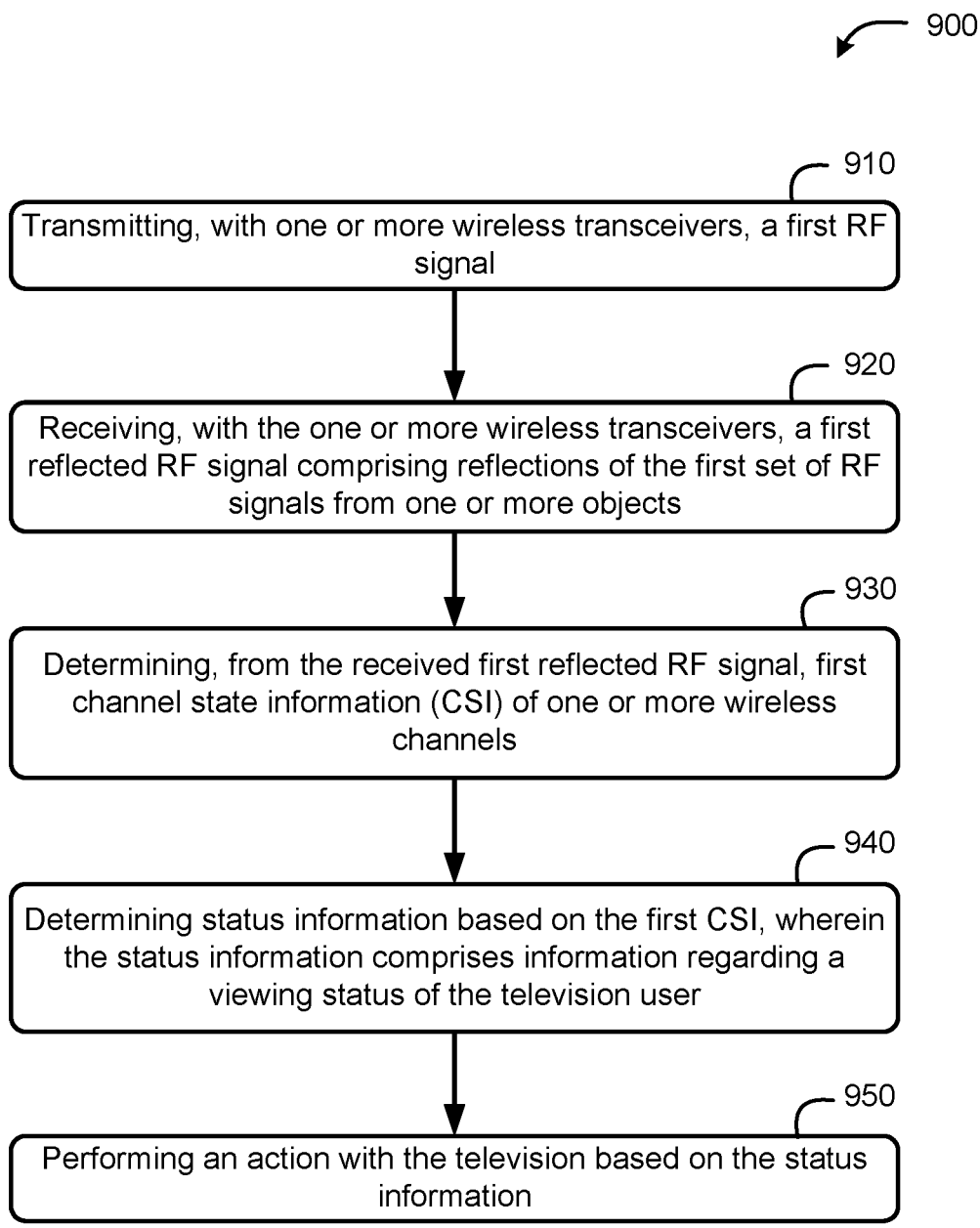
FIG. 9 is a flow diagram illustrating a method 900 of RF sensing of a television user, according to an embodiment.

FIG. 9 is a flow diagram illustrating a method 900 of RF sensing of a television user, according to an embodiment. The operations shown in the blocks of FIG. 9 may be performed by television or connected device using one or more transceivers operating as an RF sensing system in the manner described above. Example components of a television or connected device capable of performing the operations of FIG. 9 are illustrated in FIG. 10 and described in more detail below. Alternative embodiments may vary from the method 900 by adding, omitting, combining, and/or rearranging the operations illustrated, and/or or by performing operations simultaneously. The method 900 describes a general process of RF sensing of a television user, encompassing many embodiments previously described. As such, the method 900 may be considered a way in which at least some aspects of the processes illustrated in FIGS. 5, 7, and 8 described above may be implemented.

At block 910, the method comprises, transmitting, with one or more wireless transceivers, a first RF signal. As noted in the embodiments above, a television environment may have one or more transceivers, where each transceiver may comprise an RF sensing system 105 (or at least a portion thereof). The one or more transceivers may comprise one or more wireless radios capable of transmitting and receiving RF signals using a WLAN standard (e.g., IEEE 902.11/Wi-Fi), and may be used by the television and/or connected device for WLAN communication in addition to RF sensing. As such, the first RF signal may comprise communication packets utilized by the WLAN standard (e.g., IEEE 802.11). As previously noted, embodiments herein may leverage existing techniques for channel estimation to obtain CSI to use for RF sensing. As noted in the IEEE 802.11 standard, for example, two repetitions of a long training sequence can used for channel estimation. Additionally or alternatively, the one or more transceivers may comprise UWB transceivers.

Means for performing the functionality of block 910 may comprise processing unit(s) 1010, bus 1005, working memory 1035, communications subsystem 1030, wireless communications interface 1033, RF sensing system 105, and/or other components as illustrated in FIG. 10 and described hereinafter. Additional means may include Tx antenna(s) 115, Tx processing circuitry 140, mux 135, processing unit 125, memory 130, and/or other components of an RF sensing system 105 as illustrated in FIG. 1 and previously described.

At block 920, the functionality comprises receiving, with one or more wireless transceivers, a first reflected RF signal comprising reflections of the first RF signal from one or more objects. In the case where multiple television users are present, for example, the one or more objects may comprise the multiple television users (among other things). Other objects can include pets, furniture, etc., which can be ignored by the television or connected device. As noted in the above embodiments, the transceiver that receives the first reflected RF signal may be the same transceiver that transmits the RF signals (e.g., as illustrated in FIG. 3), or may be a different transceiver (e.g., as illustrated in FIG. 2). As such, according to some embodiments of the method 900, the one or more wireless transceivers may comprise a single wireless transceiver located at a single location. Alternatively, a first wireless transceiver of the one or more wireless transceivers transmits the first RF signal, and a second wireless transceiver of the one or more wireless transceivers receives the first reflected RF signal, and the first wireless transceiver is located at a different location than the second wireless transceiver. For embodiments in which more than one transceiver is used, one or more processors internal and/or external to the television may coordinate the transmission and reception of the RF signals. Additionally or alternatively, the transceivers may communicate with each other (e.g., in accordance with a governing wireless standard) to coordinate the transmission and reception of the RF signals.

Means for performing the functionality of block 920 may comprise processing unit(s) 1010, bus 1005, working memory 1035, communications subsystem 1030, wireless communications interface 1033, RF sensing system 105, and/or other components as illustrated in FIG. 10 and described hereinafter. Additional means may include Rx antenna(s) 120, Rx processing circuitry 145, mux 135, processing unit 125, memory 130, and/or other components of an RF sensing system 105 as illustrated in FIG. 1 and previously described.

The functionality at block 930 comprises determining, from the received first reflected RF signal, first CSI of one or more wireless channels. As noted, this may be determined using channel estimation techniques of a governing wireless standard for the one or more wireless transceivers that receive the reflected RF signals. Moreover, as further noted, reflected RF signals may be received by multiple antennas and/or at multiple times. Thus, in some embodiments, this may allow for the determination of not only the presence of motion or an object, but a direction as well. This may be dependent on how RF signals are transmitted and received (e.g., using low-resolution or high-resolution detection).

Means for performing the functionality of block 930 may comprise processing unit(s) 1010, bus 1005, working memory 1035, communications subsystem 1030, wireless communications interface 1033, RF sensing system 105, and/or other components as illustrated in FIG. 10 and described hereinafter. Additional means may include processing unit 125, memory 130, and/or other components of an RF sensing system 105 as illustrated in FIG. 1 and previously described.

At block 940, the functionality comprises determining status information based on the first CSI, wherein the status information comprises information regarding a viewing status of a television user. The viewing status of a television user may comprise the presence or absence of any television user or a particular television user, e.g. in a particular region of the television environment. The viewing status of the television user may comprise an identity of a television user present in the television environment, e.g. in terms of an association with a particular user profile. In some aspects, the viewing status of the television user may comprise a state of motion, a head orientation, an eyeball orientation, a sitting position, or a pose, or any combination thereof. Further, at block 950, the functionality comprises performing an action with the television based on the status information. The type of status information obtained and action performed at blocks 940 and 950 may vary, depending on the type of functionality to be implemented. As noted in the previously-described embodiments, this can include user interest determination, automatic powering down of the television, and/or automatic powering up of the television. As noted, status information regarding a television user can be based on RF sensing data, which can comprise the CSI and/or information (detected movement, volume, eyeball position, etc.) derived from the CSI.

In some embodiments, such as the embodiment illustrated in FIG. 5, status information may comprise a level of attentiveness of the television user. The level of attentiveness may be quantified as described with respect to FIGS. 6A-6C. That is, according to alternative embodiments, the method 900 may rather comprise determining the television is playing content of a predetermined type, wherein the transmitting the first RF signal is responsive to the determination that the television is playing the content of the predetermined type, and determining the status information comprises determining a level of attentiveness of the television user viewing the content, based on the first CSI. According to some embodiments, determining the level of attentiveness of the television user viewing the content comprises determining, based on the first CSI, one or more attributes of the television user while the television is playing. These attributes may comprise a head orientation, an eyeball orientation, a sitting position, or a pose, or any combination thereof. According to some embodiments, determining the one or more attributes of the television user comprises comparing information obtained based on the first CSI with stored profile information regarding the television user. According to some embodiments, performing the action with the television comprises sending, from the television, an indication of the level of attentiveness to a server of a service provider, a server of a content provider, or both. As previously noted, this level of attentiveness can be indicated in a viewership log, such as the ones illustrated in FIGS. 6A-6C.

Additionally or alternatively, as indicated in the embodiment illustrated in FIG. 7, status information may be used to implement an automatic power-down functionality. Accordingly, some embodiments of the method 900 may further comprise determining, based on the first CSI, a lack of detected movement, responsive to determining the lack of movement, transmitting, with the one or more wireless transceivers, a second RF signal, and receiving, with the one or more wireless transceivers, a second reflected RF signal comprising reflections of the second RF signal from the one or more objects. These embodiments may further comprise determining, from the received second reflected RF signal, second CSI. In such embodiments, determining the status information can be further based on the second CSI, wherein the status information comprises an indication that the television user is not watching the television, and performing the action with the television comprises powering down the television. According to some embodiments, the status information may comprise information indicative that the television user is no longer detected or the television user is no longer awake. As noted in the above-described embodiments, different types of RF sensing modes (e.g., high-resolution RF sensing and low-resolution RF sensing) may be utilized to obtain different degrees of RF sensing data. Thus, according to some embodiments, the first RF signal maybe transmitted in accordance with a first transmission mode, and the second RF signal is transmitted in accordance with a second transmission mode. In these embodiments, the second transmission mode may have a shorter transmission periodicity than the first transmission mode, a larger transmission bandwidth than the first transmission mode, or a larger number of spatial streams, or any combination thereof. Finally, embodiments of the method 900 may further include, prior to powering down the television, saving a position in content played by the television.

Additionally or alternatively, as indicated in the embodiment illustrated in FIG. 8, status information may be used to implement an automatic power-up functionality. For example, according to some embodiments, the method 900 may further comprise determining, based on the first CSI, a detected movement; responsive to determining the movement, transmitting, with the one or more wireless transceivers, a second RF signal; and receiving, with the one or more wireless transceivers, a second reflected RF signal comprising reflections of the second RF signal from the one or more objects. The embodiment may further comprise determining, from the received second reflected RF signal, second CSI, and determining the status information may be further based on the second CSI, wherein the status information comprises an indication that the television user intends to watch the television. Moreover, performing the action with the television may comprise powering up the television. As noted in the above-described embodiments, a user may assume a "power up" pose or similar position showing attentiveness to the television to cause the television to automatically power up in this manner, and these positions can be saved in RF sensing data stored in a user profile. As such, according to some embodiments, determining the television user intends to watch the television may be based at least in part on comparing information obtained from the second CSI with stored profile information regarding the television user. Here again, the functionality may include low-resolution and high-resolution RF scanning modes. As such, according to some embodiments, the first RF signal is transmitted in accordance with a first transmission mode, and the second RF signal is transmitted in accordance with a second transmission mode. In such instances, the second transmission mode may have a shorter transmission periodicity than the first transmission mode, a larger transmission bandwidth than the first transmission mode, or a larger number of spatial streams, or any combination thereof. Other embodiments enabling power up functionality may include functions such as obtaining a saved position in content played by the television and resuming playback of the content by the television from the saved position. Additionally or alternatively, embodiments may include identifying the television user based at least in part on the second CSI, determining a corresponding stored user profile for the television user based on the identity of the television user, and providing a user menu on the television, wherein content within the user menu is based at least in part on the corresponding stored user profile. According to some embodiments, identifying the television user may comprise determining the television user to be a child, and providing the user menu may comprise providing a menu for children.

Finally, embodiments may additionally or alternatively include one of the following features. According to some embodiments, the status information may comprise an indication of whether the television user was detected, an identity of the television user, an indication of whether the television user was watching content played by the television, or any combination thereof. According to some embodiments, the method 900 may further comprise determining an identity of the television user by comparing information obtained based on the first CSI with stored profile information regarding the television user. These and other features may be facilitated through an initial calibration. Thus, according to some embodiments, the method 900 may further comprise, prior to transmitting the first RF signal, performing calibration for the television user in which, while the television user is in a location for watching the television, a second RF signal is transmitted by the one or more wireless transceivers and a second reflected RF signal comprising reflections of the second RF signal from the television user are received by the one or more wireless transceivers. In such embodiments, second CSI may be determined from the received second reflected RF signal, one or more user attributes of the television user may be determined based at least in part on the second CSI, and the one or more user attributes may be stored in a user profile.

Means for performing the functionality of blocks 940 and 950 may comprise processing unit(s) 1010, bus 1005, working memory 1035, communications subsystem 1030, wireless communications interface 1033, RF sensing system 105, and/or other components as illustrated in FIG. 10 and described hereinafter. Additional means may include processing unit 125, memory 130, and/or other components of an RF sensing system 105 as illustrated in FIG. 1 and previously described.

FIG. 10 is a block diagram of an embodiment of an electronic device 1000, which may incorporate an RF sensing system 105 that can be operated in the manner discussed in the previously-described embodiments. As noted, an RF sensing system 105 may be included in each of one or more transceivers, which may be incorporated into one or more subsystems of the electronic device, such as the wireless communications interface 1033. The electronic device itself may comprise a television, set-top box, streaming device, or other device capable of performing RF sensing as described herein. It should be noted that FIG. 10 is meant only to provide a generalized illustration of various components, any or all of which may be utilized as appropriate. FIG. 10, therefore, broadly illustrates how individual system elements may be implemented in a relatively separated or relatively more integrated manner. In addition, it can be noted that components illustrated by FIG. 10 can be localized to a single device and/or distributed among various networked devices, which may be located at different physical locations. For example, some components may be internal to a television, while other components may be external to a television (while communicatively coupled with internal components via an HDMI or USB port, for example).

The electronic device 1000 is shown comprising hardware elements that can be electrically coupled via a bus 1005 (or may otherwise be in communication, as appropriate). The hardware elements may include processing unit(s) 1010, which can include without limitation one or more general-purpose processors, one or more special-purpose processors (such as a DSP, graphics processing unit (GPU), application-specific integrated circuit (ASIC), field-programmable gate array (FPGA), and/or the like), and/or other processing structure, which can be configured to perform one or more of the methods described herein, including the method described in relation to FIG. 9 and/or the processes described in FIGS. 5, 7, and 8. The electronic device 1000 also can include one or more input devices 1015, which can include without limitation a remote control, touch interface, microphone, buttons, switches, dials, and/or the like. The or more output devices 1020 can include without limitation a display, HDMI output and/or other media interface, a speaker, and/or the like.

The electronic device 1000 may further include (and/or be in communication with) one or more non-transitory storage devices 1025, which can comprise, without limitation, local and/or network accessible storage, and/or can include, without limitation, a disk drive, a drive array, an optical storage device, a solid-state storage device (such as a random access memory (RAM) and/or a read-only memory (ROM)), which can be programmable, flash-updateable, and/or the like. Such storage devices may be configured to implement any appropriate data stores, including without limitation, various file systems, database structures, and/or the like.

The electronic device 1000 may also include a communications subsystem 1030, which can include support of wireline communication technologies and/or wireless communication technologies (in some embodiments) managed and controlled by a wireless communication interface 1033. The communications subsystem 1030 may include a modem, a network card (wireless or wired), an infrared communication device, a wireless communication device, and/or a chipset, and/or the like. The communications subsystem 1030 may include one or more input and/or output communication interfaces, such as the wireless communication interface 1033 or a wired communication interface, to permit data and signaling to be exchanged with a network, mobile devices (e.g., via mobile phone apps), other computer systems, and/or any other electronic devices described herein. As previously noted, an RF sensing system 105 (as illustrated in FIG. 1) may be incorporated into a wireless communications interface 1033 such that Tx antenna(s) 115 and Rx antenna(s) 120, and the circuitry connected with the antenna elements (e.g., the other components of the RF sensing system 105), may be used for both RF sensing and data communication. For example, in some embodiments, the wireless communication interface 1033 may comprise an 802.11ad-compatible and/or 802.11ay-compatible modem capable of both RF sensing and data communication. Aspects of the wireless communication interface 1033 having an RF sensing system 105 may correspond to transceivers illustrated in FIGS. 2 and 3 and described elsewhere herein.

As noted, some embodiments may have an RF sensing system 105 that is not used for wireless communication, and may therefore be a dedicated system for RF sensing. In such instances, the RF sensing system 105 may be incorporated elsewhere within the electronic device 1000. In some embodiments, for example, the RF sensing system 105 may be incorporated into the electronic device 1000 as an input device 1015. Other sensors, too, may be included as input devices 1015.

In many embodiments, the electronic device 1000 will further comprise a working memory 1035, which can include a RAM and/or or ROM device. Software elements, shown as being located within the working memory 1035, can include an operating system 1040, device drivers, executable libraries, and/or other code, such as application(s) 1045, which may comprise computer programs provided by various embodiments, and/or may be designed to implement methods, and/or configure systems, provided by other embodiments, as described herein. Merely by way of example, one or more procedures described with respect to the method(s) discussed above, such as the methods described in relation to FIG. 9, may be implemented as code and/or instructions that are stored (e.g. temporarily) in working memory 1035 and are executable by a computer (and/or a processing unit within a computer such as processing unit(s) 1010); in an aspect, then, such code and/or instructions can be used to configure and/or adapt a general purpose computer (or other device) to perform one or more operations in accordance with the described methods.

A set of these instructions and/or code might be stored on a non-transitory computer-readable (or machine-readable) storage medium, such as the storage device(s) 1025 described above. In some cases, the storage medium might be incorporated within a computer system, such as electronic device 1000. In other embodiments, the storage medium might be separate from the electronic device 1000 (e.g., a removable medium, such as an optical disc), and/or provided in an installation package, such that the storage medium can be used to program, configure, and/or adapt a general purpose computer or electronic device with the instructions/code stored thereon. These instructions might take the form of executable code, which is executable by the electronic device 1000 and/or might take the form of source and/or installable code, which, upon compilation and/or installation on the electronic device 1000 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

With reference to the appended figures, components that can include memory can include non-transitory machine-readable media. The term "machine-readable medium" and "computer-readable medium" as used herein, refer to any storage medium that participates in providing data that causes a machine to operate in a specific fashion. In embodiments provided hereinabove, various machine-readable media might be involved in providing instructions/code to processing units and/or other device(s) for execution. Additionally or alternatively, the machine-readable media might be used to store and/or carry such instructions/code. In many implementations, a computer-readable medium is a physical and/or tangible storage medium. Such a medium may take many forms, including but not limited to, non-volatile media and volatile media. Common forms of computer-readable media include, for example, magnetic and/or optical media, any other physical medium with patterns of holes, a RAM, a programmable ROM (PROM), erasable PROM (EPROM), a FLASH-EPROM, any other memory chip or cartridge, a carrier wave as described hereinafter, or any other medium from which a computer can read instructions and/or code.

The methods, systems, and devices discussed herein are examples. Various embodiments may omit, substitute, or add various procedures or components as appropriate. For instance, features described with respect to certain embodiments may be combined in various other embodiments. Different aspects and elements of the embodiments may be combined in a similar manner. The various components of the figures provided herein can be embodied in hardware and/or software. Also, technology evolves and, thus, many of the elements are examples that do not limit the scope of the disclosure to those specific examples.

It has proven convenient at times, principally for reasons of common usage, to refer to such signals as bits, information, values, elements, symbols, characters, variables, terms, numbers, numerals, or the like. It should be understood, however, that all of these or similar terms are to be associated with appropriate physical quantities and are merely convenient labels. Unless specifically stated otherwise, as is apparent from the discussion above, it is appreciated that throughout this Specification discussions utilizing terms such as "processing," "computing," "calculating," "determining," "ascertaining," "identifying," "associating," "measuring," "performing," or the like refer to actions or processes of a specific apparatus, such as a special purpose computer or a similar special purpose electronic computing device. In the context of this Specification, therefore, a special purpose computer or a similar special purpose electronic computing device is capable of manipulating or transforming signals, typically represented as physical electronic, electrical, or magnetic quantities within memories, registers, or other information storage devices, transmission devices, or display devices of the special purpose computer or similar special purpose electronic computing device.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AA, AAB, AABBCCC, etc.

Having described several embodiments, various modifications, alternative constructions, and equivalents may be used without departing from the scope of the disclosure. For example, the above elements may merely be a component of a larger system, wherein other rules may take precedence over or otherwise modify the application of the various embodiments. Also, a number of steps may be undertaken before, during, or after the above elements are considered. Accordingly, the above description does not limit the scope of the disclosure.

In view of this description embodiments may include different combinations of features. Implementation examples are described in the following numbered clauses:

Clause 1. A method of radio frequency (RF) sensing of a television user, the method comprising: transmitting, with one or more wireless transceivers, a first RF signal; receiving, with the one or more wireless transceivers, a first reflected RF signal comprising reflections of the first RF signal from one or more objects; determining, from the received first reflected RF signal, first channel state information (CSI) of one or more wireless channels; determining status information based on the first CSI, wherein the status information comprises information regarding a viewing status of the television user; and performing an action with a television based on the status information.

Clause 2. The method of clause 1, further comprising determining the television is playing content of a predetermined type, wherein: the transmitting the first RF signal is responsive to the determining that the television is playing the content of the predetermined type; and determining the status information comprises determining a level of attentiveness of the television user viewing the content, based on the first CSI.

Clause 3. The method of clause 2, wherein determining the level of attentiveness of the television user viewing the content comprises determining, based on the first CSI, one or more attributes of the television user while the television is playing, the one or more attributes comprising: a head orientation, an eyeball orientation, a sitting position, or a pose, or any combination thereof.

Clause 4. The method of clause 3, wherein determining the one or more attributes of the television user comprises comparing information obtained based on the first CSI with stored profile information regarding the television user.

Clause 5. The method of any of clauses 1-4, wherein performing the action with the television comprises sending, from the television, an indication of the level of attentiveness to: a server of a service provider, a server of a content provider, or both.

Clause 6. The method of any of clauses 1-5, further comprising determining an identity of the television user by comparing information obtained from the first CSI with stored profile information regarding the television user.

Clause 7. The method of any of clauses 1, 5, or 6, further comprising: determining, based on the first CSI, a lack of detected movement; responsive to determining the lack of movement, transmitting, with the one or more wireless transceivers, a second RF signal; receiving, with the one or more wireless transceivers, a second reflected RF signal comprising reflections of the second RF signal from the one or more objects; and determining, from the received second reflected RF signal, second CSI; wherein: determining the status information is further based on the second CSI, wherein the status information comprises an indication that the television user is not watching the television; and performing the action with the television comprises powering down the television.

Clause 8. The method of clause 7, wherein the status information comprises information indicative that the television user is no longer detected or the television user is no longer awake.

Clause 9. The method of any clause 7 or 8, wherein: the first RF signal is transmitted in accordance with a first transmission mode; and the second RF signal is transmitted in accordance with a second transmission mode, wherein the second transmission mode has: a shorter transmission periodicity than the first transmission mode, a larger transmission bandwidth than the first transmission mode, or a larger number of spatial streams, or any combination thereof.

Clause 10. The method of any of clauses 7-9, further comprising, prior to powering down the television, saving a position in content played by the television.

Clause 11. The method of any of clauses 7-10, further comprising: determining, based on the first CSI, a detected movement; responsive to determining the movement, transmitting, with the one or more wireless transceivers, a second RF signal; receiving, with the one or more wireless transceivers, a second reflected RF signal comprising reflections of the second RF signal from the one or more objects; and determining, from the received second reflected RF signal, second CSI; wherein: determining the status information is further based on the second CSI, wherein the status information comprises an indication that the television user intends to watch the television; and performing the action with the television comprises powering up the television.

Clause 12. The method of any of clauses 1, 5, 6, or 11, further comprising determining the television user to intends to watch the television based at least in part on comparing information obtained from the second CSI with stored profile information regarding the television user.

Clause 13. The method of clause 11 or 12, wherein: the first RF signal is transmitted in accordance with a first transmission mode; and the second RF signal is transmitted in accordance with a second transmission mode, wherein the second transmission mode has: a shorter transmission periodicity than the first transmission mode, a larger transmission bandwidth than the first transmission mode, or a larger number of spatial streams, or any combination thereof.

Clause 14. The method of any of clauses 11-13, further comprising: obtaining a saved position in content played by the television; and resuming playback of the content by the television from the saved position.

Clause 15. The method of any of clauses 11-14, further comprising: identifying the television user based at least in part on the second CSI; determining a corresponding stored user profile for the television user based on an identity of the television user; and providing a user menu on the television, wherein content within the user menu is based at least in part on the corresponding stored user profile.

Clause 16. The method of any of clauses 11-15, wherein: identifying the television user comprises determining the television user to be a child; and providing the user menu comprises providing a menu for children.

Clause 17. The method of any of clauses 1-16, wherein the status information comprises: an indication of whether the television user was detected, an identity of the television user, an indication of whether the television user was watching content played by the television, or any combination thereof.

Clause 18. The method of any of clauses 1-17, further comprising, prior to transmitting the first RF signal: performing calibration for the television user in which, while the television user is in a location for watching the television: a second RF signal is transmitted by the one or more wireless transceivers, and a second reflected RF signal comprising reflections of the second RF signal from the television user are received by the one or more wireless transceivers; and wherein: second CSI is determined from the received second reflected RF signal; one or more user attributes of the television user are determined based at least in part on the second CSI; and the one or more user attributes are stored in a user profile.

Clause 19. The method of any of clauses 1-18, a first wireless transceiver of the one or more wireless transceivers transmits the first RF signal, and a second wireless transceiver of the one or more wireless transceivers receives the first reflected RF signal, and wherein the first wireless transceiver is located at a different location than the second wireless transceiver.

Clause 20. The method of any of clauses 1-19, wherein the one or more wireless transceivers comprise one or more Wireless Local Area Network (WLAN) or Wi-Fi transceivers.

Clause 21. A device for radio frequency (RF) sensing of a television user, the device comprising: one or more wireless transceivers; a memory; and one or more processing units communicatively coupled with the one or more wireless transceivers and the memory, the one or more processing units configured to: transmit, with one or more wireless transceivers, a first RF signal; receive, with the one or more wireless transceivers, a first reflected RF signal comprising reflections of the first RF signal from one or more objects; determine, from the received first reflected RF signal, first channel state information (CSI) of one or more wireless channels; determine status information based on the first CSI, wherein the status information comprises information regarding a viewing status of the television user; and perform an action with a television based on the status information.

Clause 22. The device of clause 21, wherein the one or more processing units are further configured to determine the television is playing content of a predetermined type, wherein: the one or more processing units are configured to transmit the first RF signal responsive to determining that the television is playing the content of the predetermined type; and to determine the status information, the one or more processing units are configured to determine a level of attentiveness of the television user viewing the content, based on the first CSI.

Clause 23. The device of clause 22, wherein, to determine a level of attentiveness of the television user viewing the content, the one or more processing units are configured to determine, based on the first CSI, one or more attributes of the television user while the television is playing, the one or more attributes comprising: a head orientation, an eyeball orientation, a sitting position, or a pose, or any combination thereof.

Clause 24. The device of clause 23, wherein, to determine the one or more attributes of the television user, the one or more processing units are configured to compare information obtained based on the first CSI with stored profile information regarding the television user.

Clause 25. The device of any of clauses 21-24, wherein, to perform the action with the television, the one or more processing units are configured to send, from the television, an indication of the level of attentiveness to: a server of a service provider, a server of a content provider, or both.

Clause 26. The device of any of clauses 21-25, wherein the one or more processing units are further configured to determine an identity of the television user by comparing information obtained from the first CSI with stored profile information regarding the television user.

Clause 27. The device of any of clauses 21, 25, or 26, wherein the one or more processing units are further configured to: determine, based on the first CSI, a lack of detected movement; responsive to determining the lack of movement, transmit, with the one or more wireless transceivers, a second RF signal; receive, with the one or more wireless transceivers, a second reflected RF signal comprising reflections of the second RF signal from the one or more objects; and determine, from the received second reflected RF signal, second CSI; wherein: the one or more processing units are configured to determine the status information further based on the second CSI, wherein the status information comprises an indication that the television user is not watching the television; and to perform the action with the television, the one or more processing units are configured to power down the television.

Clause 28. The device of clause 27, wherein the status information comprises information indicative that the television user is no longer detected or the television user is no longer awake.

Clause 29. The device of clause 27 or 28, wherein: the one or more processing units are configured to transmit the first RF signal in accordance with a first transmission mode; and the one or more processing units are configured to transmit the second RF signal in accordance with a second transmission mode, wherein the second transmission mode has: a shorter transmission periodicity than the first transmission mode, a larger transmission bandwidth than the first transmission mode, or a larger number of spatial streams, or any combination thereof.

Clause 30. The device of any of clauses 27-29, wherein the one or more processing units are further configured to, prior to powering down the television, save a position in content played by the television in the memory.

Clause 31. The device of any of clauses 27-30, wherein the one or more processing units are further configured to: determine, based on the first CSI, a detected movement; responsive to determining the movement, transmit, with the one or more wireless transceivers, a second RF signal; receive, with the one or more wireless transceivers, a second reflected RF signal comprising reflections of the second RF signal from the one or more objects; and determine, from the received second reflected RF signal, second CSI; wherein: the one or more processing units are configured to determine the status information further based on the second CSI, wherein the status information comprises an indication that the television user intends to watch the television; and to perform the action with the television, the one or more processing units are configured power up the television.

Clause 32. The device of any of clauses 21, 25, 26, or 31, wherein the one or more processing units are further configured to determine the television user to intends to watch the television based at least in part on comparing information obtained from the second CSI with stored profile information regarding the television user.

Clause 33. The device of clause 31 or 32, wherein: the one or more processing units are configured to transmit the first RF signal in accordance with a first transmission mode; and the one or more processing units are configured to transmit the second RF signal in accordance with a second transmission mode, wherein the second transmission mode has: a shorter transmission periodicity than the first transmission mode, a larger transmission bandwidth than the first transmission mode, or a larger number of spatial streams, or any combination thereof.

Clause 34. The device of any of clauses 31-33, wherein the one or more processing units are further configured to: obtain a saved position in content played by the television; and resume playback of the content by the television from the saved position.

Clause 35. The device of any of clauses 31-34, wherein the one or more processing units are further configured to: identify the television user based at least in part on the second CSI; determine a corresponding stored user profile for the television user based on an identity of the television user; and provide a user menu on the television, wherein content within the user menu is based at least in part on the corresponding stored user profile.

Clause 36. The device of any of clauses 31-35, wherein: to identify the television user, the one or more processing units are configured to determine the television user to be a child; and to provide the user menu, the one or more processing units are configured to provide a menu for children.

Clause 37. The device of any of clauses 31-36, wherein the status information comprises: an indication of whether the television user was detected, an identity of the television user, an indication of whether the television user was watching content played by the television, or any combination thereof.

Clause 38. The device of any of clauses 21-37, wherein the one or more processing units are further configured to, prior to transmitting the first RF signal: perform calibration for the television user in which, while the television user is in a location for watching the television, the one or more processing units are configured to: transmit a second RF signal by the one or more wireless transceivers, and receive, by the one or more wireless transceivers, a second reflected RF signal comprising reflections of the second RF signal from the television user; and wherein the one or more processing units are configured to: determine second CSI from the received second reflected RF signal; determine one or more user attributes of the television user based at least in part on the second CSI; and store the one or more user attributes in a user profile in the memory.

Clause 39. The device of any of clauses 21-38, wherein the one or more processing units are further configured to: transmit the first RF signal using a first wireless transceiver of the one or more wireless transceivers, and receive the first reflected RF signal using a second wireless transceiver of the one or more wireless transceivers, and wherein the first wireless transceiver is located at a different location than the second wireless transceiver.

Clause 40. The device of any of clauses 21-39, wherein the one or more wireless transceivers comprise one or more Wireless Local Area Network (WLAN) or Wi-Fi transceivers.

Clause 41. A device for of radio frequency (RF) sensing of a television user, the device comprising: means for transmitting a first RF signal; means for receiving a first reflected RF signal comprising reflections of the first RF signal from one or more objects; means for determining, from the received first reflected RF signal, first channel state information (CSI) of one or more wireless channels; means for determining status information based on the first CSI, wherein the status information comprises information regarding a viewing status of the television user; and means for performing an action with a television based on the status information.

Clause 42. The device of clause 41, further comprising means for determining the television is playing content of a predetermined type, wherein: transmitting the first RF signal is responsive to the determining that the television is playing the content of the predetermined type; and determining the status information comprises determining a level of attentiveness of the television user viewing the content, based on the first CSI.

Clause 43. The device of clause 41 or 42, further comprising means for determining an identity of the television user by comparing information obtained from the first CSI with stored profile information regarding the television user.

Clause 44. The device of any of clauses 41-43, further comprising: means for determining, based on the first CSI, a lack of detected movement; means for transmitting a second RF signal responsive to determining the lack of movement; means for receiving a second reflected RF signal comprising reflections of the second RF signal from the one or more objects; and means for determining, from the received second reflected RF signal, second CSI; wherein: determining the status information is further based on the second CSI, wherein the status information comprises an indication that the television user is not watching the television; and performing the action with the television comprises powering down the television.

Clause 45. The device of any of clauses 41-44, further comprising: means for determining, based on the first CSI, a detected movement; means for transmitting a second RF signal responsive to determining the movement; means for receiving a second reflected RF signal comprising reflections of the second RF signal from the one or more objects; and means for determining, from the received second reflected RF signal, second CSI; wherein: determining the status information is further based on the second CSI, wherein the status information comprises an indication that the television user intends to watch the television; and performing the action with the television comprises powering up the television.

Clause 46. The device of any of clauses 41-45, further comprising: means for performing calibration for the television user in which, while the television user is in a location for watching the television: a second RF signal is transmitted by the device, and a second reflected RF signal comprising reflections of the second RF signal from the television user are received by the device; and wherein: second CSI is determined from the received second reflected RF signal; one or more user attributes of the television user are determined based at least in part on the second CSI; and the one or more user attributes are stored in a user profile.

Clause 47. The device of any of clauses 41-46, wherein: the means for transmitting the first RF signal comprise a first wireless transceiver, and the means for receiving the first reflected RF signal comprise a second wireless transceiver.

Clause 48. The device of any of clauses 41-47, wherein the first wireless transceiver is located at a different location than the second wireless transceiver.

Clause 49. The device of any of clauses 41-48, wherein the first wireless transceiver, the second wireless transceiver, or both, comprise a Wireless Local Area Network (WLAN) or Wi-Fi transceiver.

Clause 50. A non-transitory computer-readable medium storing instructions for radio frequency (RF) sensing of a television user, the instructions comprising code for: transmitting, with one or more wireless transceivers, a first RF signal; receiving, with the one or more wireless transceivers, a first reflected RF signal comprising reflections of the first RF signal from one or more objects; determining, from the received first reflected RF signal, first channel state information (CSI) of one or more wireless channels; determining status information based on the first CSI, wherein the status information comprises information regarding a viewing status of the television user; and performing an action with a television based on the status information.

What is claimed is:

1. A method of radio frequency (RF) sensing of a television user, the method comprising:
    transmitting, with one or more wireless transceivers, a first RF signal;
    receiving, with the one or more wireless transceivers, a first reflected RF signal comprising reflections of the first RF signal from one or more objects;
    determining, from the received first reflected RF signal, first channel state information (CSI) of one or more wireless channels;
    determining, based on the first CSI, a lack of detected movement;
    responsive to determining the lack of movement, transmitting, with the one or more wireless transceivers, a second RF signal;
    receiving, with the one or more wireless transceivers, a second reflected RF signal comprising reflections of the second RF signal from the one or more objects; and
    determining, from the received second reflected RF signal, second CSI;
    determining status information based on the first CSI and the second CSI, wherein the status information comprises information regarding a viewing status of the television user; and
    performing an action with a television based on the status information.

2. The method of claim 1, further comprising determining the television is playing content of a predetermined type, wherein:
    the transmitting the first RF signal is responsive to the determining that the television is playing the content of the predetermined type; and
    determining the status information comprises determining a level of attentiveness of the television user viewing the content.

3. The method of claim 2, wherein determining the level of attentiveness of the television user viewing the content comprises determining one or more attributes of the television user while the television is playing, the one or more attributes comprising:
    a head orientation,
    an eyeball orientation,
    a sitting position, or
    a pose, or
    any combination thereof.

4. The method of claim 3, wherein determining the one or more attributes of the television user comprises comparing information obtained with stored profile information regarding the television user.

5. The method of claim 2, wherein performing the action with the television comprises sending, from the television, an indication of the level of attentiveness to:
    a server of a service provider,
    a server of a content provider,
    or both.

6. The method of claim 1, further comprising determining an identity of the television user by comparing information obtained from the first CSI with stored profile information regarding the television user.

7. The method of claim 1,
wherein the status information comprises an indication that the television user is not watching the television; and
performing the action with the television comprises powering down the television.

8. The method of claim 7, wherein the status information comprises information indicative that the television user is no longer detected or the television user is no longer awake.

9. The method of claim 7, wherein:
the first RF signal is transmitted in accordance with a first transmission mode; and
the second RF signal is transmitted in accordance with a second transmission mode, wherein the second transmission mode has:
a shorter transmission periodicity than the first transmission mode,
a larger transmission bandwidth than the first transmission mode, or
a larger number of spatial streams, or
any combination thereof.

10. The method of claim 7, further comprising, prior to powering down the television, saving a position in content played by the television.

11. The method of claim 1, wherein the status information comprises:
an indication of whether the television user was detected,
an identity of the television user,
an indication of whether the television user was watching content played by the television, or
any combination thereof.

12. The method of claim 1, further comprising, prior to transmitting the first RF signal:
performing calibration for the television user in which, while the television user is in a location for watching the television:
a second RF signal is transmitted by the one or more wireless transceivers, and
a second reflected RF signal comprising reflections of the second RF signal from the television user are received by the one or more wireless transceivers;
and wherein:
second CSI is determined from the received second reflected RF signal;
one or more user attributes of the television user are determined based at least in part on the second CSI; and
the one or more user attributes are stored in a user profile.

13. The method of claim 1, a first wireless transceiver of the one or more wireless transceivers transmits the first RF signal, and a second wireless transceiver of the one or more wireless transceivers receives the first reflected RF signal, and wherein the first wireless transceiver is located at a different location than the second wireless transceiver.

14. The method of claim 1, wherein the one or more wireless transceivers comprise one or more Wireless Local Area Network (WLAN) or Wi-Fi transceivers.

15. A device for radio frequency (RF) sensing of a television user, the device comprising:
one or more wireless transceivers;
a memory; and
one or more processing units communicatively coupled with the one or more wireless transceivers and the memory, the one or more processing units configured to:
transmit, with one or more wireless transceivers, a first RF signal;
receive, with the one or more wireless transceivers, a first reflected RF signal comprising reflections of the first RF signal from one or more objects;
determine, from the received first reflected RF signal, first channel state information (CSI) of one or more wireless channels;
determine, based on the first CSI, a lack of detected movement;
responsive to determining the lack of movement, transmit, with the one or more wireless transceivers, a second RF signal;
receive, with the one or more wireless transceivers, a second reflected RF signal comprising reflections of the second RF signal from the one or more objects; and
determine, from the received second reflected RF signal, second CSI;
determine status information based on the first CSI and the second CSI, wherein the status information comprises information regarding a viewing status of the television user; and
perform an action with a television based on the status information.

16. The device of claim 15, wherein the one or more processing units are further configured to determine the television is playing content of a predetermined type, wherein:
the one or more processing units are configured to transmit the first RF signal responsive to determining that the television is playing the content of the predetermined type; and
to determine the status information, the one or more processing units are configured to determine a level of attentiveness of the television user viewing the content.

17. The device of claim 16, wherein, to determine a level of attentiveness of the television user viewing the content, the one or more processing units are configured to determine one or more attributes of the television user while the television is playing, the one or more attributes comprising:
a head orientation,
an eyeball orientation,
a sitting position, or
a pose, or
any combination thereof.

18. The device of claim 17, wherein, to determine the one or more attributes of the television user, the one or more processing units are configured to compare information obtained with stored profile information regarding the television user.

19. The device of claim 16, wherein, to perform the action with the television, the one or more processing units are configured to send, from the television, an indication of the level of attentiveness to:
a server of a service provider,
a server of a content provider,
or both.

20. The device of claim 15, wherein the one or more processing units are further configured to determine an identity of the television user by comparing information obtained from the first CSI with stored profile information regarding the television user.

21. The device of claim 15, wherein the status information comprises an indication that the television user is not watching the television; and
to perform the action with the television, the one or more processing units are configured to power down the television.

22. The device of claim 21, wherein the status information comprises information indicative that the television user is no longer detected or the television user is no longer awake.

23. The device of claim 21, wherein:
the one or more processing units are configured to transmit the first RF signal in accordance with a first transmission mode; and
the one or more processing units are configured to transmit the second RF signal in accordance with a second transmission mode, wherein the second transmission mode has:
a shorter transmission periodicity than the first transmission mode,
a larger transmission bandwidth than the first transmission mode, or
a larger number of spatial streams, or
any combination thereof.

24. The device of claim 21, wherein the one or more processing units are further configured to, prior to powering down the television, save a position in content played by the television in the memory.

25. The device of claim 15, wherein the status information comprises:
an indication of whether the television user was detected,
an identity of the television user,
an indication of whether the television user was watching content played by the television, or
any combination thereof.

26. The device of claim 15, wherein the one or more processing units are further configured to, prior to transmitting the first RF signal:
perform calibration for the television user in which, while the television user is in a location for watching the television, the one or more processing units are configured to:
transmit a second RF signal by the one or more wireless transceivers, and
receive, by the one or more wireless transceivers, a second reflected RF signal comprising reflections of the second RF signal from the television user;
and wherein the one or more processing units are configured to:
determine second CSI from the received second reflected RF signal;
determine one or more user attributes of the television user based at least in part on the second CSI; and
store the one or more user attributes in a user profile in the memory.

27. The device of claim 15, wherein the one or more processing units are further configured to:
transmit the first RF signal using a first wireless transceiver of the one or more wireless transceivers, and
receive the first reflected RF signal using a second wireless transceiver of the one or more wireless transceivers, and
wherein the first wireless transceiver is located at a different location than the second wireless transceiver.

28. The device of claim 27, wherein the first wireless transceiver, the second wireless transceiver, or both, comprise a Wireless Local Area Network (WLAN) or Wi-Fi transceiver.

29. The device of claim 15, wherein the one or more wireless transceivers comprise one or more Wireless Local Area Network (WLAN) or Wi-Fi transceivers.

30. A device for of radio frequency (RF) sensing of a television user, the device comprising:
means for transmitting a first RF signal;
means for receiving a first reflected RF signal comprising reflections of the first RF signal from one or more objects;
means for determining, from the received first reflected RF signal, first channel state information (CSI) of one or more wireless channels;
means for determining, based on the first CSI, a lack of detected movement;
means for transmitting a second RF signal responsive to determining the lack of movement:
means for receiving a second reflected RF signal comprising reflections of the second RF signal from the one or more objects; and
means for determining, from the received second reflected RF signal, second CSI;
means for determining status information based on the first CSI and the second CSI, wherein the status information comprises information regarding a viewing status of the television user; and
means for performing an action with a television based on the status information.

31. The device of claim 30, further comprising means for determining the television is playing content of a predetermined type, wherein:
transmitting the first RF signal is responsive to the determining that the television is playing the content of the predetermined type; and
determining the status information comprises determining a level of attentiveness of the television user viewing the content.

32. The device of claim 30, further comprising means for determining an identity of the television user by comparing information obtained from the first CSI with stored profile information regarding the television user.

33. The device of claim 30, CSI;
wherein the status information comprises an indication that the television user is not watching the television; and
the means for performing the action with the television comprises means for powering down the television.

34. The device of claim 30, further comprising:
means for performing calibration for the television user in which, while the television user is in a location for watching the television:
a second RF signal is transmitted by the device, and
a second reflected RF signal comprising reflections of the second RF signal from the television user are received by the device;
and wherein:
second CSI is determined from the received second reflected RF signal;
one or more user attributes of the television user are determined based at least in part on the second CSI; and
the one or more user attributes are stored in a user profile.

35. The device of claim 30, wherein:
the means for transmitting the first RF signal comprise a first wireless transceiver, and
the means for receiving the first reflected RF signal comprise a second wireless transceiver.

36. The device of claim 35, wherein the first wireless transceiver is located at a different location than the second wireless transceiver.

37. A non-transitory computer-readable medium storing instructions for radio frequency (RF) sensing of a television user, the instructions comprising code for:
- transmitting, with one or more wireless transceivers, a first RF signal;
- receiving, with the one or more wireless transceivers, a first reflected RF signal comprising reflections of the first RF signal from one or more objects;
- determining, from the received first reflected RF signal, first channel state information (CSI) of one or more wireless channels;
- determining, based on the first CSI, a lack of detected movement;
- responsive to determining the lack of movement, transmitting, with the one or more wireless transceivers, a second RF signal;
- receiving, with the one or more wireless transceivers, a second reflected RF signal comprising reflections of the second RF signal from the one or more objects; and
- determining, from the received second reflected RF signal, second CSI;
- determining status information based on the first CSI and the second CSI, wherein the status information comprises information regarding a viewing status of the television user; and
- performing an action with a television based on the status information.

* * * * *